(12) United States Patent
Updyke et al.

(10) Patent No.: US 9,714,918 B2
(45) Date of Patent: Jul. 25, 2017

(54) ELECTROPHORESIS GEL CASSETTE AND COMB

(71) Applicant: LIFE TECHNOLOGIES CORPORATION, Carlsbad, CA (US)

(72) Inventors: Timothy Updyke, Temecula, CA (US); Jennifer Miller, Oceanside, CA (US); Thomas Diller, San Diego, CA (US); Siddharth Kannan, Valencia, CA (US); Robert Bennett, Encinitas, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 14/158,696

(22) Filed: Jan. 17, 2014

(65) Prior Publication Data

US 2014/0231260 A1    Aug. 21, 2014

Related U.S. Application Data

(63) Continuation of application No. 12/862,460, filed on Aug. 24, 2010, now abandoned.

(60) Provisional application No. 61/236,293, filed on Aug. 24, 2009, provisional application No. 61/236,795, filed on Aug. 25, 2009, provisional application No. 61/237,287, filed on Aug. 26, 2009, provisional application No. 61/237,195, filed on Aug. 26, 2009.

(51) Int. Cl.
   *G01N 27/447*    (2006.01)

(52) U.S. Cl.
   CPC .. *G01N 27/44721* (2013.01); *G01N 27/44778* (2013.01)

(58) Field of Classification Search
None
See application file for complete search history.

(56) References Cited

U.S. PATENT DOCUMENTS

| | | |
|---|---|---|
| 3,620,947 A | 11/1971 | Allen et al. |
| D231,609 S | 5/1974 | Broek et al. |
| 4,164,464 A | 8/1979 | Allington et al. |
| 4,294,684 A | 10/1981 | Sewer |
| D282,352 S | 1/1986 | Hoefer et al. |
| 4,608,146 A | 8/1986 | Penaluna |
| 4,773,984 A | 9/1988 | Flesher et al. |
| 4,795,541 A | 1/1989 | Hurd et al. |
| 4,810,348 A | 3/1989 | Sarrine et al. |
| 4,830,725 A | 5/1989 | Berninger et al. |

(Continued)

FOREIGN PATENT DOCUMENTS

| | | |
|---|---|---|
| EP | 1371085 | 12/2003 |
| WO | 96/13717 A1 | 5/1996 |

(Continued)

OTHER PUBLICATIONS

Alvarez, et al., "Genetic Diversity of *Mycobacterium avium* Isolates Recovered from Clinical Samples and from the Environment: Molecular Characterization for Diagnostics Purposes", *Journal of Clinical Microbiology*, vol. 46, No. 4, Feb. 13, 2008; pp. 1246-1251.

(Continued)

*Primary Examiner* — J. Christopher Ball

(57) ABSTRACT

Provided herein is an apparatus for gel electrophoresis comprising a cassette and a comb having at least one wedge-shaped tooth.

18 Claims, 28 Drawing Sheets

(56) References Cited

U.S. PATENT DOCUMENTS

| | | | |
|---|---|---|---|
| D303,007 S | | 8/1989 | Flesher et al. |
| D315,952 S | | 4/1991 | Berninger et al. |
| 5,073,246 A | | 12/1991 | Chu et al. |
| 5,147,522 A | | 9/1992 | Sarrine et al. |
| 5,284,565 A | * | 2/1994 | Chu et al. ............... 204/619 |
| 5,318,682 A | | 6/1994 | Singer |
| 5,338,426 A | | 8/1994 | Shigeura et al. |
| 5,407,552 A | | 4/1995 | Lebacq |
| 5,411,657 A | | 5/1995 | Leka |
| 5,460,709 A | | 10/1995 | Sarrine et al. |
| 5,514,255 A | | 5/1996 | Gautsch |
| 5,569,369 A | | 10/1996 | Leffler et al. |
| 5,618,399 A | | 4/1997 | Gautsch et al. |
| 5,626,735 A | | 5/1997 | Chu et al. |
| 5,627,022 A | | 5/1997 | Renfrew et al. |
| 5,632,877 A | | 5/1997 | Van Atta |
| 5,656,145 A | | 8/1997 | Nguyen et al. |
| 5,685,967 A | * | 11/1997 | Manis et al. ............... 204/616 |
| 5,785,835 A | | 7/1998 | Saito et al. |
| 5,799,773 A | | 9/1998 | Heffelfinger et al. |
| 5,800,691 A | | 9/1998 | Kozulic |
| 5,891,314 A | | 4/1999 | Heffelfinger et al. |
| 5,897,760 A | | 4/1999 | Heffelfinger et al. |
| 5,951,838 A | | 9/1999 | Heffelfinger et al. |
| 5,972,188 A | | 10/1999 | Rice et al. |
| 5,993,628 A | | 11/1999 | Selby et al. |
| 6,063,250 A | | 5/2000 | Becker |
| D430,304 S | | 8/2000 | Oonuma et al. |
| 6,110,344 A | | 8/2000 | Renfrew et al. |
| 6,139,709 A | | 10/2000 | Scott |
| 6,231,813 B1 | | 5/2001 | Ally et al. |
| 6,413,402 B1 | | 7/2002 | Manusu et al. |
| 6,521,111 B1 | | 2/2003 | Amshey |
| D516,733 S | | 3/2006 | Pedraza et al. |
| D524,948 S | | 7/2006 | Pedraza et al. |
| D564,378 S | | 3/2008 | Kaushal et al. |
| D564,924 S | | 3/2008 | Kaushal et al. |
| D667,134 S | | 9/2012 | Updyke et al. |
| 9,400,260 B2 | | 7/2016 | Suh |
| 2002/0079222 A1 | | 6/2002 | Sevigny et al. |
| 2003/0089607 A1 | * | 5/2003 | Rivern Rojas et al. ...... 204/458 |
| 2007/0056854 A1 | * | 3/2007 | Latham ............ G01N 27/44704 204/606 |
| 2007/0102298 A1 | | 5/2007 | Riveron Rojas et al. |
| 2008/0272002 A1 | | 11/2008 | Johansen et al. |
| 2011/0042217 A1 | | 2/2011 | Updyke et al. |
| 2011/0114487 A1 | | 5/2011 | Schmidt et al. |
| 2013/0175172 A1 | | 7/2013 | Updyke |

FOREIGN PATENT DOCUMENTS

| | | |
|---|---|---|
| WO | 98/16820 A1 | 4/1998 |
| WO | 98/25136 | 6/1998 |
| WO | 99/54721 A1 | 10/1999 |
| WO | 01/16589 A1 | 3/2001 |
| WO | 2008/119332 | 10/2008 |
| WO | 2011/028532 | 3/2011 |

OTHER PUBLICATIONS

Bartos, "Identification of members of *Mycobaterium avium* species by Accu-Probes, serotyping, and single IS900, IS901, IS1245 and IS901-flanking region PCR with internal standards", *Journal Microbiological Methods*, vol. 64, 2006; pp. 333-345.

Bio-Rad, "Automating electrophoresis with the new Experion (TM) System", *BioRadiations*, vol. 115, Jan. 1, 2005; pp. 2-3.

Cayrou, et al., "Genotyping of Mycobacterium avium complex organisms using multispacer sequence typing", *Microbiology*, vol. 156, No. 3, Mar. 1, 2010; pp. 687-694.

Covert, et al., "Occurrence of nontuberculous *Mycobacteria* in environmental samples", *Applied and Environmental Microbiology*, vol. 65, No. 5, Jun. 1999; pp. 2492-2496.

EP10814246.4; European Search Report mailed Feb. 4, 2013; 11 pages.

Falkinham, et al., "Factors influencing numbers of *Mycobacterium avium*, *Mycobacterium intracellulare*, and other *Mycobacteria* in drinking water distribution systems", *Applied and Environmenta Microbiology*, vol. 67, No. 3, Jun. 2001; pp. 1225-1231.

Higgins, et al., "Identification of *Mycobacterium* spp. of veterinary importance using rpOB gene sequencing", *BMC Veterinary Research*, vol. 7, No. 1, Jan. 1, 2011; pp. 1-14.

Hilborn, et al., "Molecular comparison of *Mycobacterium avium* isolates from clinical and environmental sources", *Applied and Environmental Microbiology*, vol. 74, No. 15, Aug. 2008; pp. 4966-4968.

Johansen, et al., "Distribution of IS1311 and IS1245 in *Mycobacterium avium* Subspecies Revisited", *Jounal of Clinical Microbiological*, vol. 45, No. 5, May 1, 2005; pp. 2500-2502.

Le Dantec, "Occurrence of *Mycobacteria* in Water Treatment Lines and in Water Distribution Systems", *Applied and Environmenta Microbiology*, vol. 68, No. 11, Nov. 2002; pp. 5318-5325.

Moravkova, et al., "A mixed infection of *Mycobacterium avium* subsp. *paratuberculosis* and *M. a hominissuis* in one red deer (*Cervus elaphus*) studied by IS900 BstEll and IS1245 Pvull RFLP analyses: a case report", *Verterinarni Medicina*, vol. 53, No. 8, 2008; pp. 445-451.

Pate, et al., "IS1245 RFLP-based genotyping study of *Mycobacterium avium* subsp. *hominissuis* isolates from pigs and humans", *Comparative Immunology, Microbiology & Infectious Diseases*, vol. 31, No. 6, Nov. 1, 2008; pp. 537-550.

PCT/US2010/46506; International Search Report and Written Opinion mailed on Oct. 15, 2010.

Phywe, "Electrophoresis chamber, Vertical. Product No. 35018-20", http://www.phywe.com/461/apg/360/pid/27438/Elektrophorese-Kammer,-vertikal-htm>., Feb. 13, 2013; 1 page.

Santos, et al., "Detection and identification of *Mycobacteria* in the Lisbon water distribution system", *Water and Science Technology*, vol. 52, No. 8, 2005; pp. 177-180.

Shin, et al., "Efficient Differentiation of *Mycobacterium avium* Complex Species and Subspecies by Use of Five-Target Multiplex PCR", *Journal of Clinical Microbiology*, vol. 48, No. 11, Nov. 2010; pp. 4057-4062.

Sigma-Aldrich Co. LLC, "TV 100 mini vertical electrophoresis unit for pre-case gels", http://ww.sigmaaldrich.com/catalog/product/sigma/z649759?lang=en&region=US>., Feb. 13, 2013; 2 pages.

\* cited by examiner

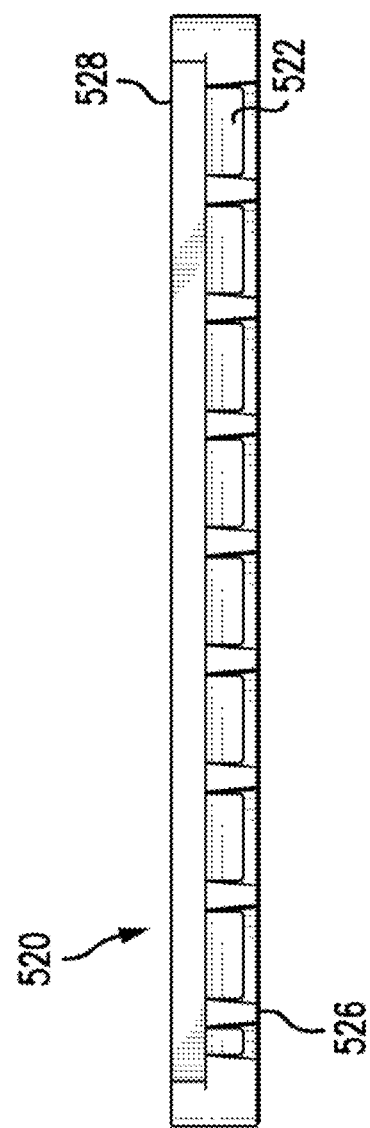

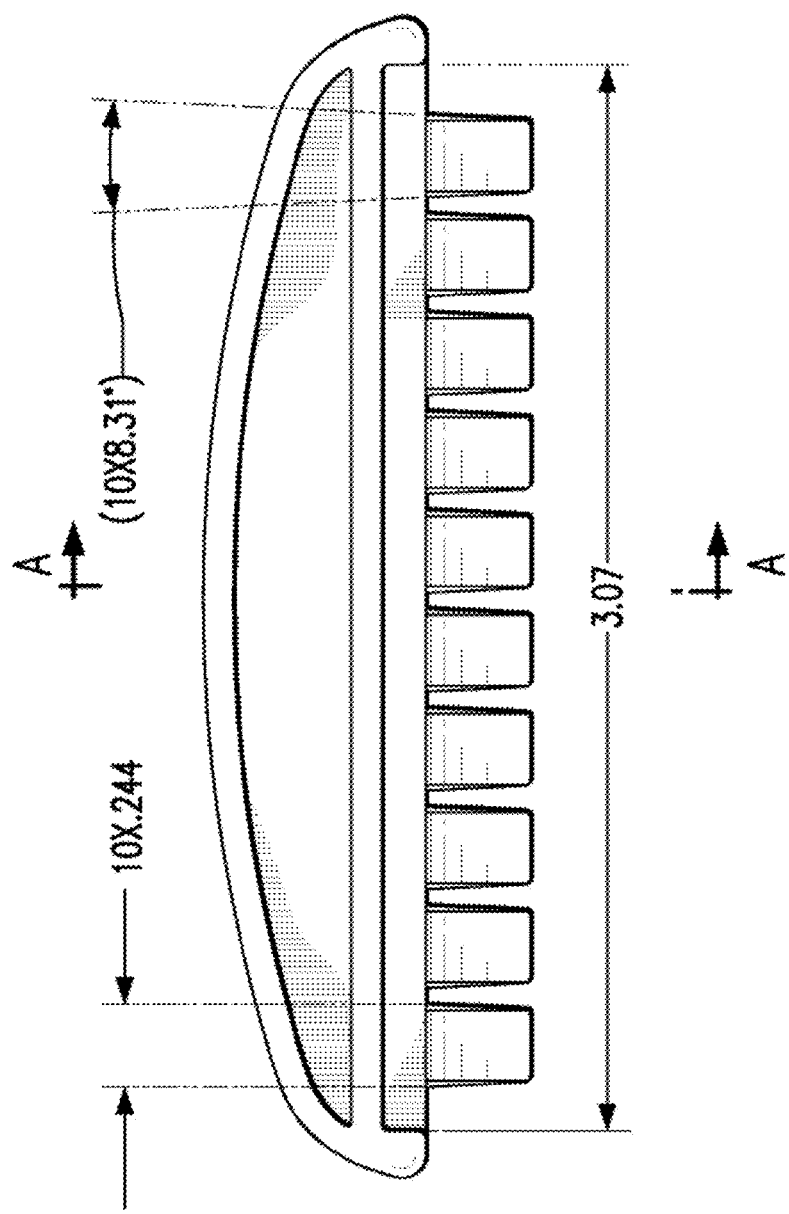

ELECTROPHORESIS GEL CASSETTE AND COMB

CROSS-REFERENCE TO RELATED APPLICATIONS

The present application is a continuation and claims the right of priority under 35 U.S.C. 120 to U.S. application Ser. No. 12/862,460, filed on Aug. 24, 2010, now abandoned, which claims a benefit under 35 U.S.C. §119(e) from earlier filed U.S. Provisional Applications Nos. 61/237,287 filed Aug. 26, 2009, 61/237,195 filed Aug. 26, 2009, 61/236,795 filed Aug. 25, 2009, and 61/236,293 filed Aug. 24, 2009, all of which are commonly owned with the present application, and all of which are hereby expressly incorporated by reference in their entirety as though fully set forth herein.

FIELD

The present invention relates to gel consumables.

BACKGROUND

Gel electrophoresis is a common procedure for the separation of biological molecules, such as DNA, RNA, polypeptides and proteins. In gel electrophoresis, the molecules are separated into bands according to the rate at which an imposed electric field causes them to migrate through a filtering gel.

The basic unit used in this technique consists of a gel enclosed in a glass tube or sandwiched as a slab between glass or plastic plates. Gels have an open molecular network structure, defining pores which are saturated with an electrically conductive buffered solution. These pores are large enough to admit passage of the migrating macromolecules through the gel.

The gel is placed in a chamber in contact with buffer solutions which make electrical contact between the gel and the cathode or anode of an electrical power supply. A sample containing the macromolecules and a tracking dye is placed on top of the gel. An electric potential is applied to the gel causing the sample macromolecules and tracking dye to migrate toward the bottom of the gel. The electrophoresis is halted just before the tracking dye reaches the end of the gel. The locations of the bands of separated macromolecules are then determined. By comparing the distance moved by particular bands in comparison to the tracking dye and macromolecules of known size, the size of other macromolecules can be determined.

Polyacrylamide gels are commonly used for electrophoresis. Other gels suitable for electrophoresis include agarose gels and starch gels. Polyacrylamide gel electrophoresis or PAGE is popular because the gels are optically transparent, electrically neutral and can be made with a range of pore sizes.

Methods of making PAGE gels are well known. See B. Hames and D. Rickwood, Gel Electrophoresis of Proteins (2d ed. Oxford University Press, 1990); A. Andrews, Electrophoresis (2nd ed. Oxford University Press, 1986). In general, stock solutions containing acrylamide monomer, a crosslinker such as bisacrylamide, gel buffers and modifying agents such as sodium dodecyl sulphate ("SDS") are prepared. These stock solutions can be stored until a gel is needed. To manufacture a gel, the stock solutions are mixed with water in proportions according to the final desired concentrations of the various constituents.

Glass has typically been used to make molds for electrophoresis gels. However, glass suffers from the disadvantage that it is fragile, difficult to form into particular shapes and expensive. It is easier and more economical to form gel molds from plastic materials by processes such as injection molding. However, using plastic molds for casting electrophoresis gels may contribute to decreased resolution of the separated macromolecule bands. Decreased resolution of the macromolecule bands may be caused by macromolecules moving faster on the surface of the gel in contact with the mold than in the interior of the gel. This variation in migration rates between the surface of the gel and the interior lead may lead to smearing of the macromolecule bands.

In addition to the decreased resolution that may occur in a gel, another disadvantage of current methods for creating and performing gels, such as SDS-PAGE gels, is that the use of the gel is limited by the amount of sample that may be loaded into the gel. It may be desirable to have the ability to apply greater volumes of samples to the gels. Therefore it may be desirable to produce gels of greater thickness or to produce gels with wells with an increased well-volume proportional to the increased thickness of the gel. However, this may lead to gels that require proportionately greater current for a given field strength. Greater current for a given field strength may lead to greater heat build up in the gels which in turn may lead to decreased resolution and performance. Another problem that may arise with thicker gels is that protein bands may transfer less efficiently in down stream applications, such as western blotting.

One solution for increasing sample volume in a gel may be to increase the depth of the wells of a particular width and gel thickness. However, the increased volumes may produce increased sample heights above the gel, leading to thicker protein band starting zones, and lower resolution. If the stacking gel height is proportionately increased, then the resolving gel length will be proportionately decreased, also contributing to reduced resolution in a given gel cassette.

Therefore, it would be beneficial to develop a gel cassette that would enable producing a gel of a particular thickness having a well capable of holding a sample volume that is at least double the well volume of the current methods, while maintaining the same sample height above the gel as a standard well of particular width and thickness.

SUMMARY

Provided herein is an apparatus for gel electrophoresis comprising: a gel cassette; and a comb having at least one wedge-shaped tooth. In some embodiments, the gel cassette may include a retainer plate and a divider plate. The gel cassette includes a lip extending from the exterior surface of at least one of the divider plate or the retainer plate. In some embodiments, the wedge-shaped tooth has a volume of at least 40 uL. In some embodiments, the cassette has at least one interior surface that may be coated with a coating. In some embodiments, the coating is an oxygen interference coating, such as, for example, at least one of SiO or $SiO_2$. In some embodiments the comb further comprises a recessed area on the comb wherein the recessed area is configured to prevent the formation of a skin in a gel during gel formation.

Further provided herein is an apparatus for gel electrophoresis comprising a comb having wedge-shaped teeth configured to create a sample well in a 1 mm gel, wherein the sample well size is at least 10% larger than a gel having a sample well created by a standard comb.

Provided herein is an apparatus for gel electrophoresis comprising a comb having wedge-shaped teeth configured to create a sample well in a 1 mm gel, wherein the sample well size is at least 100% larger than a gel having a sample well created by a standard comb. In some embodiments, the sample well created by a standard mini gel ten teeth comb has a volume of 37.5 µL.

Further provided herein is an apparatus for gel electrophoresis comprising a ten teeth mini gel comb having wedge-shaped teeth configured to create a sample well in a 1 mm gel, wherein the sample well has a volume of at least 70 µL.

An apparatus for gel electrophoresis comprising a comb having wedge-shaped teeth configured to create sample wells configured to receive at least 10% more sample than a standard gel sample well. In some embodiments, the apparatus is configured to create a gel having sharp bands. In some embodiments, the apparatus is configured to create a gel having high resolution.

Provided herein is an apparatus for gel electrophoresis comprising: a gel cassette having a lip extending at an angle from at least one exterior surface of the cassette; and a comb having at least one wedge-shaped tooth.

Further provided herein is an apparatus for gel electrophoresis comprising a gel cassette having a cavity; and a comb; and at least one tooth located on the comb, the at least one tooth having at least one side that is slanted, wherein the at least one tooth is located at least 0.335 inches from the edge of the cavity.

Provided herein is an apparatus for gel electrophoresis comprising a comb having wedge-shaped teeth configured to create sample wells configured to receive at least 10% more sample than a standard gel sample well. In some embodiments, the device may be configured to create a gel that isolates the desired component as a sharp band or a high resolution band or both.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Some of the novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 5A-5C show various views of an embodiment of a comb;

FIGS. 10A-10C are a side view, a cross-sectional view, and a bottom view, respectively, of a ten well comb according to various embodiments of the present teachings;

FIGS. 11A-1 IC are a side view, a cross-sectional view, and a bottom view, respectively, of a twelve well comb according to various embodiments of the present teachings;

DETAILED DESCRIPTION

Figure 1:
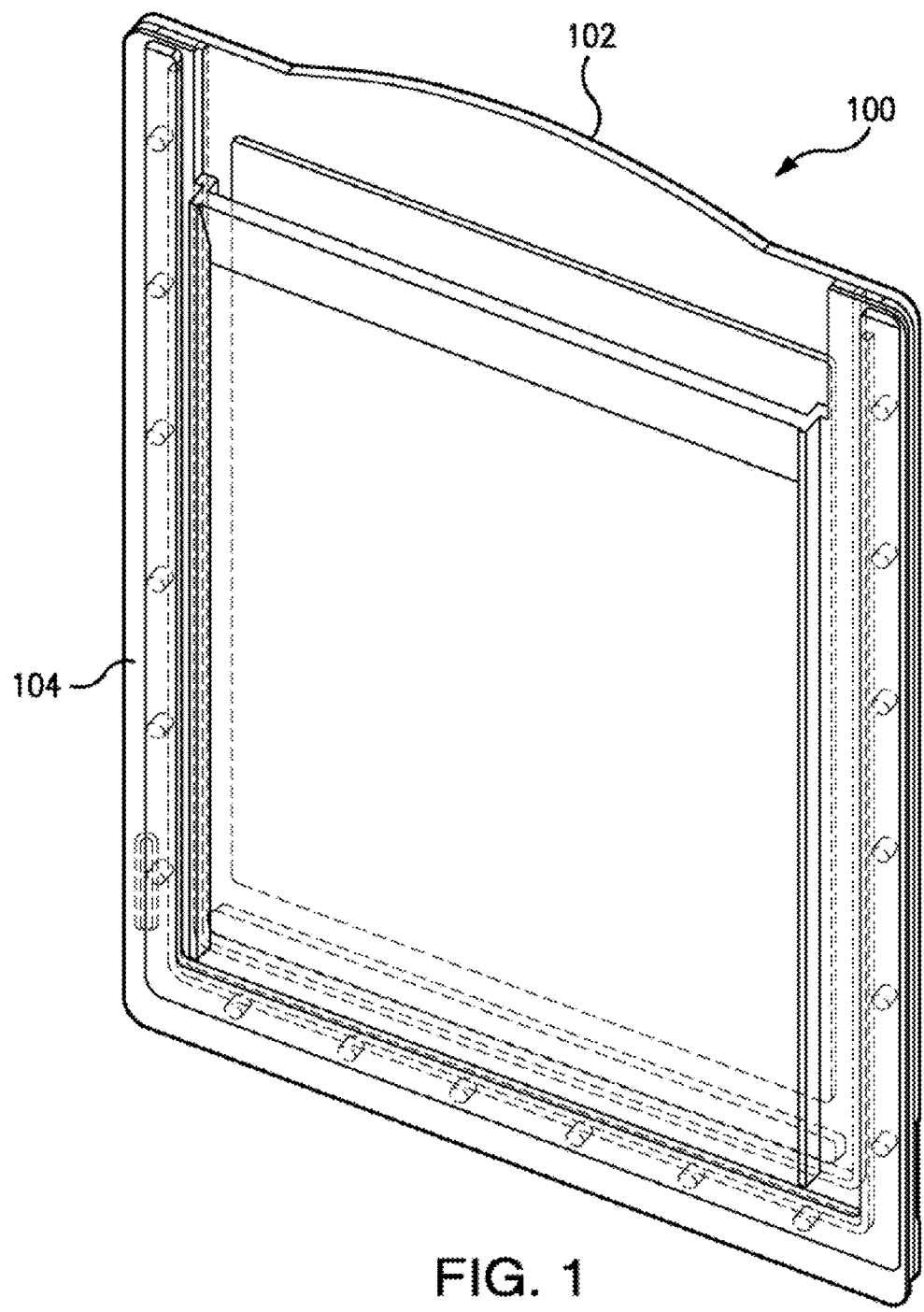
FIG. 1 shows an embodiment of an assembled gel cassette according to various embodiments of the present teachings.

Provided herein is an apparatus for gel electrophoresis comprising a gel cassette and a comb having at least one wedge-shaped tooth. The gel cassette may include a retainer plate and a divider plate. The plates may be formed by a process such as injection molding. Any suitable plastic may be used for forming the plates, such as for example purposes only polymers such as polyethylene terephthalate, polyvinyl chloride, polymethyl methacrylate, polystyrene, polyethylene, polymethyl polypropylene, and cellulose acetates or various co-polymers. In some embodiments, the plastic may be a transparent plastic so that the gel may be viewed inside the assembled cassette. In some embodiments, the cassette may be constructed from glass plates, or may be constructed from one glass plate and one plastic plate. In some embodiments, the device may be configured to create precast gels that lay flat on various surfaces. The ability to create precast gels that lay flat may be beneficial for product shipping and storage, as well as during routine handling by the user. Additionally, the gel cassette may lay flat in auto-loading machinery during gel manufacturing.

In some embodiments, the divider plate has a series of features, bumps, or posts located along the length of either the sides of the plate, along the bottom length of the plate or both along the sides and bottom of the plate. The posts may function as energy directors during the assembly process to create a uniform seal around the plate. In some embodiments, a slot may be located at the bottom portion of the divider plate, and in some embodiments, may or may not extend through the thickness of the plate. The slot may expose the gel inside the cassette to a buffer, such as an anode buffer, to complete or assist in completing an electrical path circuit during electrophoresis. During formation of the gel, the slot may be sealed with a sealant, such as tape, epoxy, polymers, conductive polymers or any other suitable sealant to prevent the gel material from escaping the assembled cassette prior to setting of the gel. In some embodiments, the divider plate may include a ridge that together with the spacer on the retainer plate creates the gel cavity. In some embodiments, the sealant may be present on the divider plate prior to assembling of the cassette, or the sealant may be placed over the slot on the assembled cassette by the user prior to filling the assembled cassette with a gel material. After the gel has be formed, the sealant may be removed if a non-conductive sealant is used, so to expose the gel to a buffer to complete or assist in completing an electrical path circuit. At the top of the divider plate, the top surface may include a grip or a curved surface to facilitate handling of the assembled cassette. In some embodiments, at least one of the plates, for example, the retainer plate may have a spacer located on its interior surface. The spacer may be any suitable shaped spacer, for example, a generally u-shaped raised spacer located on the interior surface. In some embodiments, the spacer may be located on the interior surface of one plate and contact the interior surface of the other plate. In some embodiments, a spacer may be located on the interior surface of both plates and the two spacers may contact each other when the cassette is formed. The spacer or spacers may further serve to help maintain the space between the divider plate and the retainer plate when the plates are joined to form a cassette. When the retainer plate and the divider plate are joined together, the interior surfaces of the plates form a slab shaped cavity which may be sealed by the raised spacer. In some embodiments, the ridge located on the divider forms the seal between the divider plate and the retainer plate. In some embodiments, both the spacer and the ridge seal the gel cavity. In some embodiments, the retainer plate and the divider plate may be fabricated as a single piece of plastic. In some embodiments, the retainer plate and the divider plate may be two separate parts that are connected together. The two separate parts may be connected together by any suitable mechanism for attaching the plates together including, for example purposes only, glue, pressure fitting, welding, adhesive, clamps, clips, or any other suitable mechanism. The thickness of the cavity may be determined by the height of the spacer. In some embodiments, the cavity formed by the divider plate and the retainer plate is capable of holding gel material that may form a gel about 1 mm thick.

In some embodiments, a lip extends at some angle away from the exterior surface of one of the plates to form an opening. Gel material may enter into the cassette through the opening. Additionally, a structure for forming sample wells in the gel may be introduced to the gel material through the opening. In some embodiments, the lip may extend from the exterior surface of one of the plates at an angle, for example at about a 70 degree angle from a plane perpendicular to the exterior surface of the plate, or 20 degrees from surface of the plate. In some embodiments, the angle may be between about 15 degrees and about 25 degrees, between about 10 degrees and 30 degrees, between about 5 degrees and 35 degrees, or any other suitable angle. In some embodiments, the lip may extend from the exterior surface of the plate by less than about 45 degrees. Projections may be located on the exterior surface of the retainer plate to support the lip. In some embodiments, the projections may also facilitate stacking the welded cassettes in a magazine, aiding in the manufacturing process. In some embodiments, an assembled cassette may have at least one lip on at least one side to create an opening that may be able to accommodate a comb for creating wells in the gel where the comb is wedge-shaped, such as any of the combs described herein. In some embodiments, a lip may be located on both sides of the opening, creating a v-shaped opening to accommodate v-shaped teeth on a comb. In some embodiments, the opening of the cassette may have an opening that is flat on both sides, but is wide enough to accommodate wedge shaped or v-shaped teeth on a comb without the need for a lip extending from one of the surfaces of the plate.

In some embodiments of the device, the cassette has at least one interior surface which may be coated with a coating. The coating may be an oxygen interference coating (a coating that forms an oxygen barrier that reduces diffusion from the surface of the plastic plates into the gel to prevent significant local variations in the rate of oxygen diffusion) such as, for example purposes only, a coating comprising $SiO_x$, SiO, or $SiO_2$. In some embodiments the coating may be substantially transparent. The interior surfaces may be coated manually or mechanically and in some embodiments where two separate plates are formed into the cassette, the coating may be performed before or after joining the plates into the cassette. In some embodiments, the interior surfaces of the cassette may be coated under vacuum using evaporation or vapor deposition, sputter deposition, chemical vapor deposition, plasma-enhanced chemical vapor deposition, or any combination thereof. In some embodiments, the coating deposited may be of a thickness less than about 5000 Angstroms in thickness.

During preparation of a gel, the slot in the divider plate may be sealed. The slot may be sealed by any suitable sealant including tape, epoxy, glue, polymer compound, or any other suitable sealant. The sealant may or may not be a conductive sealant. In some embodiments, the sealant may be a permanent sealant or a removable sealant. Once the slot has been sealed, the cassette may be held vertically and gel-forming mixture is poured through the opening into the cavity formed between the retainer plate and the divider plate. The gel mixture may be in contact with the interior surfaces of the divider plate and the retainer plate.

Further provided herein is an apparatus for gel electrophoresis comprising a comb having wedge-shaped teeth configured to create a sample well in a 1 mm gel, wherein the sample well size is at least about 10% larger than a gel having a sample well created by a standard comb. In some embodiments, the sample well size created by a standard comb in 37.5 µL. In some embodiments, the sample well size created by the wedge well comb may be at least 4.1 µL. In some embodiments, the sample well size created by the wedge well may be at least about 50 µL, at least 60 µL, at least about 70 µL, at least about 75 µL.

Provided herein is an apparatus for gel electrophoresis comprising a comb having wedge-shaped teeth configured to create sample wells configured to receive at least 10% more sample than a standard gel sample well. Increased sample size may allow for more sample to be loaded into the gel without causing damage to the gel and yet still produce sharp, high resolution bands. Additionally, a large sample well opening may facilitate loading samples with standard pipette tips instead of special drawn-out gel loading pipette tips.

Once the gel material for forming a gel has been poured into the opening of an assembled cassette, a comb may be inserted into the opening of the assembled cassette and into the gel material. The depth of insertion of the comb may be limited by the edges of the comb and the shoulders of the opening located on the cassette. In some embodiments, the depth of insertion of the comb may be further limited by the comb resting on the front edge of the lip. Once the gel has been cast, the comb may then be removed leaving a void in the gel at the position of each tooth. Each void forms a sample well having a sample volume.

In some embodiments, the comb may have wedge-shaped teeth. A comb having wedge-shaped teeth may be capable of creating wedge-shaped wells in the gel. In some embodiments, the wedge-shaped teeth have flat surfaces at the tips of the teeth. The flat bottom surface of the teeth creates sample wells having flat bottoms. The flat bottom of the sample well becomes the leading edge of the stacked sample bands which may ultimately resolve into bands that are as flat and similar to bands created by standard combs. The wedge-shaped wells created by insertion of the comb with wedge shaped teeth into the gel material may provide a larger opening to the well at the top of the sample well and thereby create easier access to the wells using a standard pipette tip on a single pipette or on a multi-channel pipette. Additionally, the wedge-shaped wells permit a greater amount of sample to be loaded into a thinner gel (for example, approximately 1 mm thick gels). The comb may be used with any of the cassettes described herein previously, or may be used with any other suitable cassette for creating a gel.

The wedge-shaped wells in the gel created by the wedge shaped teeth may be of a volume at least 10% greater than the volume of the wells created using a standard comb. In some embodiments, a standard comb may create wells having a volume of about 37.5 μL. In some embodiments, the wedge shaped wells may have a volume that is at least 20% greater, at least 50% greater, at least 100% greater, at least 150% greater, at least 175% greater, at least 200% greater, at least 250% greater than a well created using a standard comb. In some embodiments, the sample well size created by the wedge well comb may be at least 41 μL. In some embodiments, the sample well size created by the wedge well may be at least about 45 μL, at least about 55 μL, at least 60 μL, at least about 70 μL, at least about 75 μL, at least about 90 μL, at least about 100 μL, at least about 110 μL, at least about 130 μL.

Additionally, the wedge-shaped wells may allow for loading an increased amount of sample while maintaining or improving band sharpness and resolution during electrophoresis while reducing edge effects. The wedge shaped design of the wells formed by the teeth of a wedge-tooth comb allows more sample to be loaded into a well, while keeping the sample away from the sides of the gel. Sample that is located toward the ends of the gel may not form as sharp bands or bands having high resolution. Positioning of the wells at such locations reduces the chance that the bands formed in the gel will turn up at the ends of the band or "smile" or turn down at the edges of the band or "frown." Additionally, the wedge-shaped wells created using the apparatus described herein have a. greater cross sectional area at the top of the sample well as compared to the bottom of the sample well. The increase in cross sectional area creates a lower voltage drop at any given constant voltage, current or wattage at the top of the sample well compared to the bottom of the sample well. The lower voltage drop, or field strength, in this area may lead to better sample stacking than in the thinner sections of the well and/or gel, or in gels with wells of the same thickness through out the sample loading volume.

In some embodiments, the gel cassettes are about 10 cm by 10 cm for mini-gel cassettes. The gels housed in the gel cassettes are about 7 cm in length (the running length) by about 8 cm wide. The gel cassettes and gels run in the gel cassettes may be any suitable length. In some embodiments, the gel cassette width may be large enough to reduce edge effects in gels having at least 10 wells. In some embodiments, the assembled cassette may include a gap that runs around the outer perimeter of the cassette. The gap may facilitate the opening of the cassette for gel retrieval. In some embodiments, the gel cassette may be opened with a gel knife or may be opened by hand.

In some embodiments, the comb may be a ten-tooth comb, that is, a comb used for forming 10 sample wells in a gel. In some embodiments, the comb may be at least a single tooth comb, at least a 2-tooth comb, at least a five-tooth comb, at least a seven-tooth comb, at least a 9-tooth comb, at least a 10-tooth comb, at least a twelve-tooth comb, at least a 15-tooth comb, at least a 17-tooth comb, at least a 20-tooth comb, or any other comb having a suitable number of teeth. In some embodiments, the comb may be molded from any suitable plastic including, but not limited to polymers such as polyethylene terephthalate, polyvinyl chloride, polymethyl methacrylate, polystyrene, polyethylene, polymethyl polypropylene, cellulose acetates, co-polymers, polycarbonate, or any other suitable material. In some embodiments, the dimensions of the teeth may be uniform along the length of the comb or the teeth may have varying dimensions along the length of the comb. The teeth may or may not be the same shape as the wedge shaped opening of the cassette.

In some embodiments, the edge of the comb opposite to the teeth may serve as a handle that may facilitate the insertion and removal of the comb from the cassette. In some embodiments, the edge may be curved. The comb may further include a back surface and a front surface. In some embodiments, the front and back surfaces are solid. In some embodiments, the front surface of the comb has a recessed space which facilitates gripping the comb by the user to facilitate the insertion of the comb into the cassette as well as to remove the comb from the cassette once the gel and wells have been formed.

I. Cassette

FIG. 1 shows an embodiment of an assembled gel cassette 100. The assembled gel cassette 100 comprises two plastic plates, a retaining plate 104 and a divider plate 102. The plates may be formed by a process such as injection molding. Any suitable plastic may be used for forming the plates 102, 104. Suitable plastics for forming electrophoresis gel molds include polymers such as polyethylene terephthalate, polyvinyl chloride, polymethyl methacrylate, polystyrene, polyethylene, polymethyl polypropylene, and cellulose acetates or various co-polymers. In some embodiments, the plastic may be a transparent plastic so that the gel may be viewed inside the assembled cassette 100. In some embodiments, the cassette 100 may be constructed from glass plates, or may be constructed from one glass plate and one plastic plate.

Figure 2A:
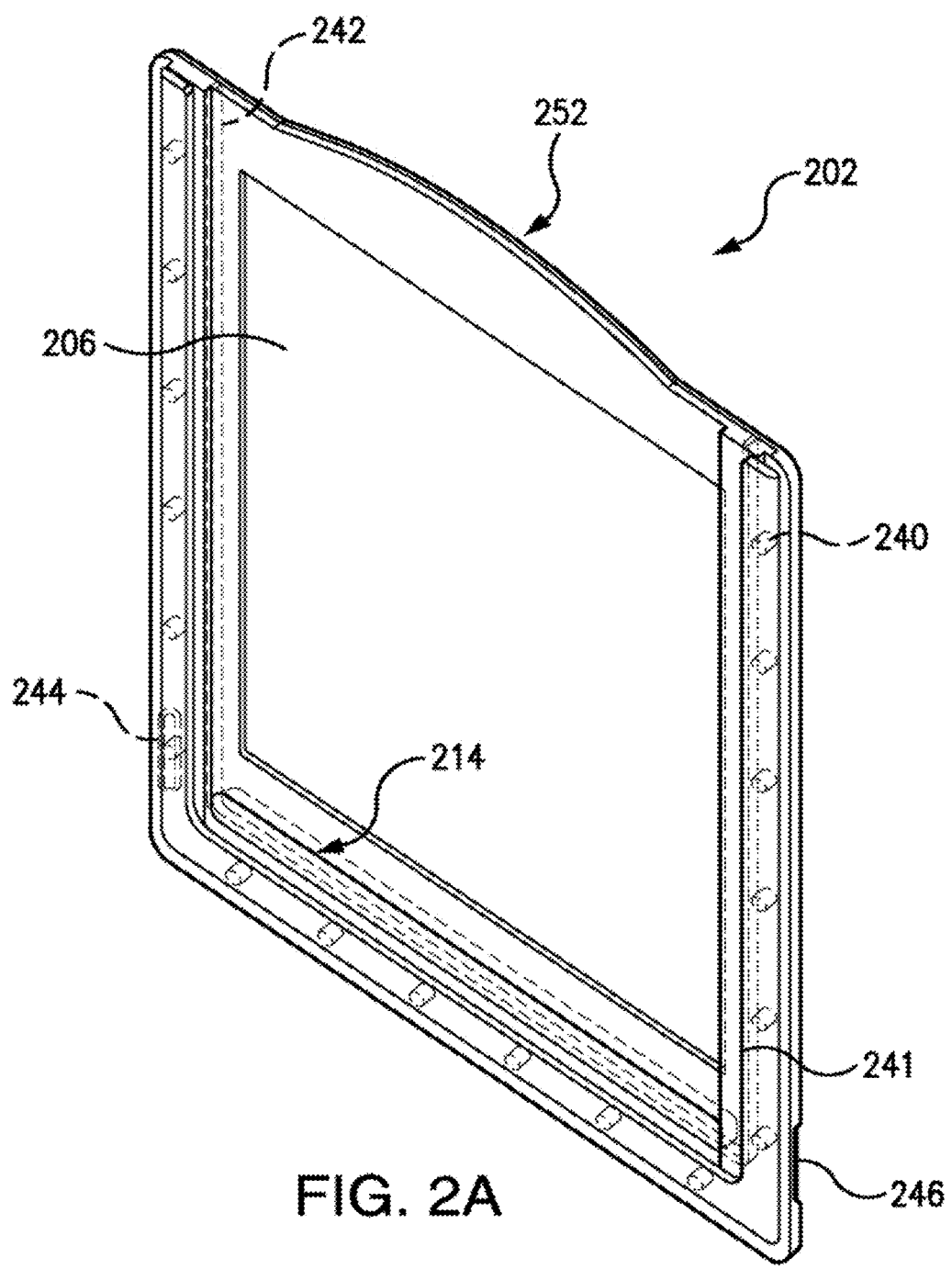
FIG. 2A shows an embodiment of a divider plate according to various embodiments of the present teachings.

Referring to FIG. 2A, one embodiment of a divider plate 202 is shown having an interior surface 206. In some embodiments, the divider plate has a series of features, bumps, or posts 240 located along the length of the sides of the plate 204 and along the bottom length of the plate. The posts 240 may protrude from the divider plate 202 and upon attachment of the divider 202 to the retainer plate (204 in FIG. 2B) the posts 240 may connect with the retainer plate. As shown in FIG. 2A, the divider plate 202 may additionally include a ridge 241 that runs down the sides and across the bottom of the divider plate 202. The ridge may be used to seal the gel cavity on the assembled cassette. In some embodiments, a slot 214 may be located at the bottom portion of the divider plate 202, and in some embodiments, may or may not extend through the thickness of the plate 204. The slot 214 may expose the gel inside the cassette to a buffer, such as an anode buffer, to complete or assist in completing an electrical path circuit during electrophoresis. On the back surface of the plate a groove 242 may or may not be present. Additionally, cut-outs 244, 246 may be located on the back surface 248 of the plate to facilitate removal of any sealant blocking the slot. At the top of the divider plate 202, the top surface 252 may include a grip or a curved surface, as shown in FIG. 2A, to facilitate handling of the assembled cassette.

Figure 2B:
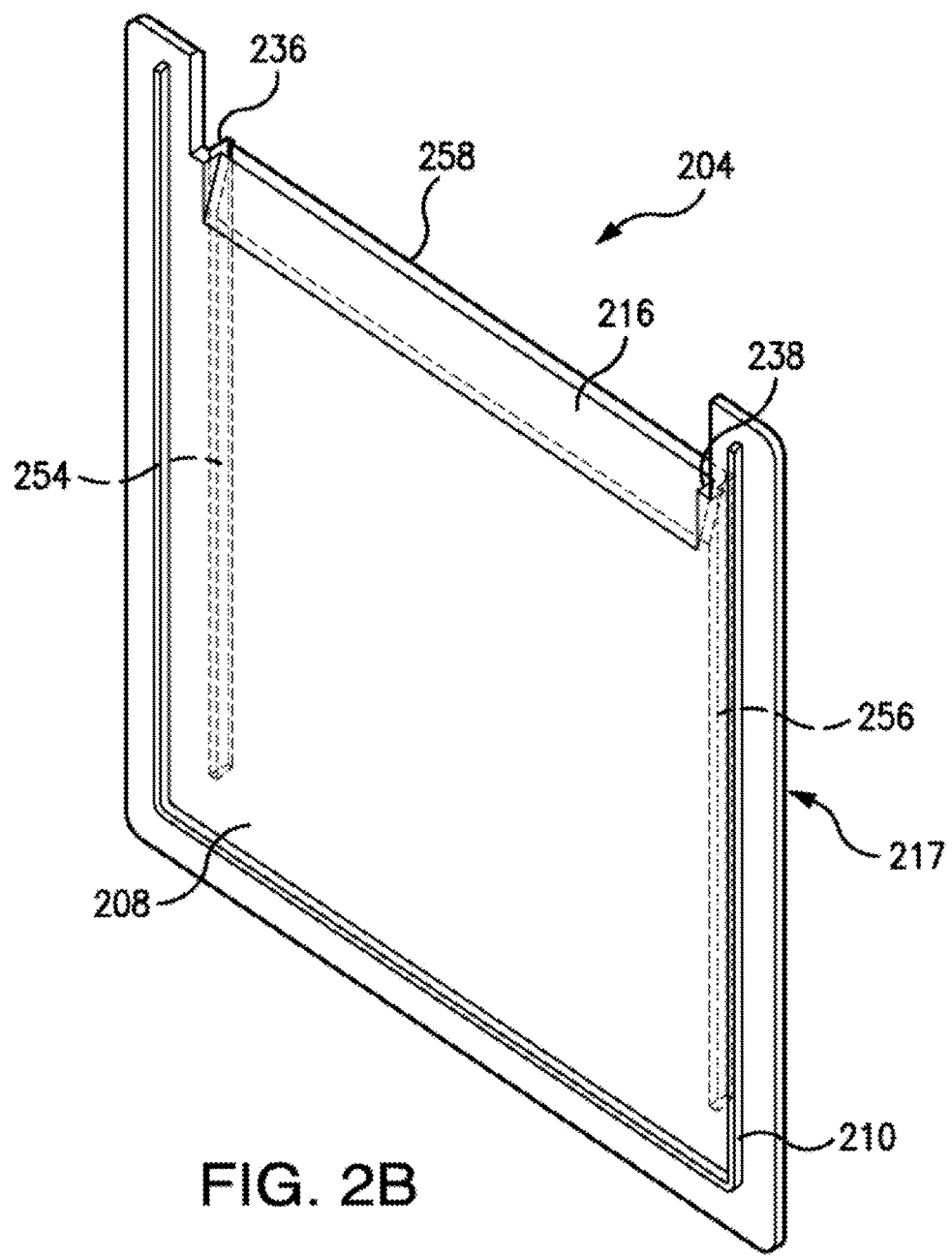
FIG. 2B shows an embodiment of a retainer plate according to various embodiments of the present teachings.

FIG. 2B shows an embodiment of a retainer plate 204 having an interior surface 208. In some embodiments, the retainer plate 204 may have a generally u-shaped raised spacer 210 located on the interior surface 208 which may contact the divider plate 202. The u-shaped spacer 210 may further serve to help dictate the spacing between or to maintain the space between the retainer plate 204 and the divider plate 202 when the plates are joined to form a cassette. When the divider plate 202 and the retainer plate 204 are joined together, the interior surfaces 206, 208 of the plates form a slab shaped cavity which may be bounded by the raised spacer 210. During assembly, either the spacer 210, the ridge 241 on the divider plate 204 (in FIG. 2B), or the spacer 210 and ridge 241 may seal the cavity. The thickness of the cavity is determined by the height of the u-shaped spacer 210. In some embodiments, the cavity formed by the divider plate 202 and the retainer plate 204 is capable of containing and confining gel material that may form a gel 1 mm thick.

In some embodiments, a lip 216 extends at some angle away from the exterior surface of one of the plates to form the opening, for example from the exterior surface 217 of the retainer plate 204 as shown in FIG. 2B. The lip further includes a first and second shoulder 236, 238, respectively, and a front edge 258. Projections 254, 256 may be located on the exterior surface 217 of the retainer plate to support the lip 216. In some embodiments, the projections 254, 256 may also facilitate stacking the welded cassettes in a magazine, aiding in the manufacturing process. In some embodiments, an assembled cassette may have at least one lip 216 on at least one side to create an opening that may be able to accommodate a comb for creating wells in the gel where the comb is wedge-shaped, such as any of the combs described herein. In some embodiments, a lip may be located on both sides of the opening, creating a v-shaped opening.

Figure 3:
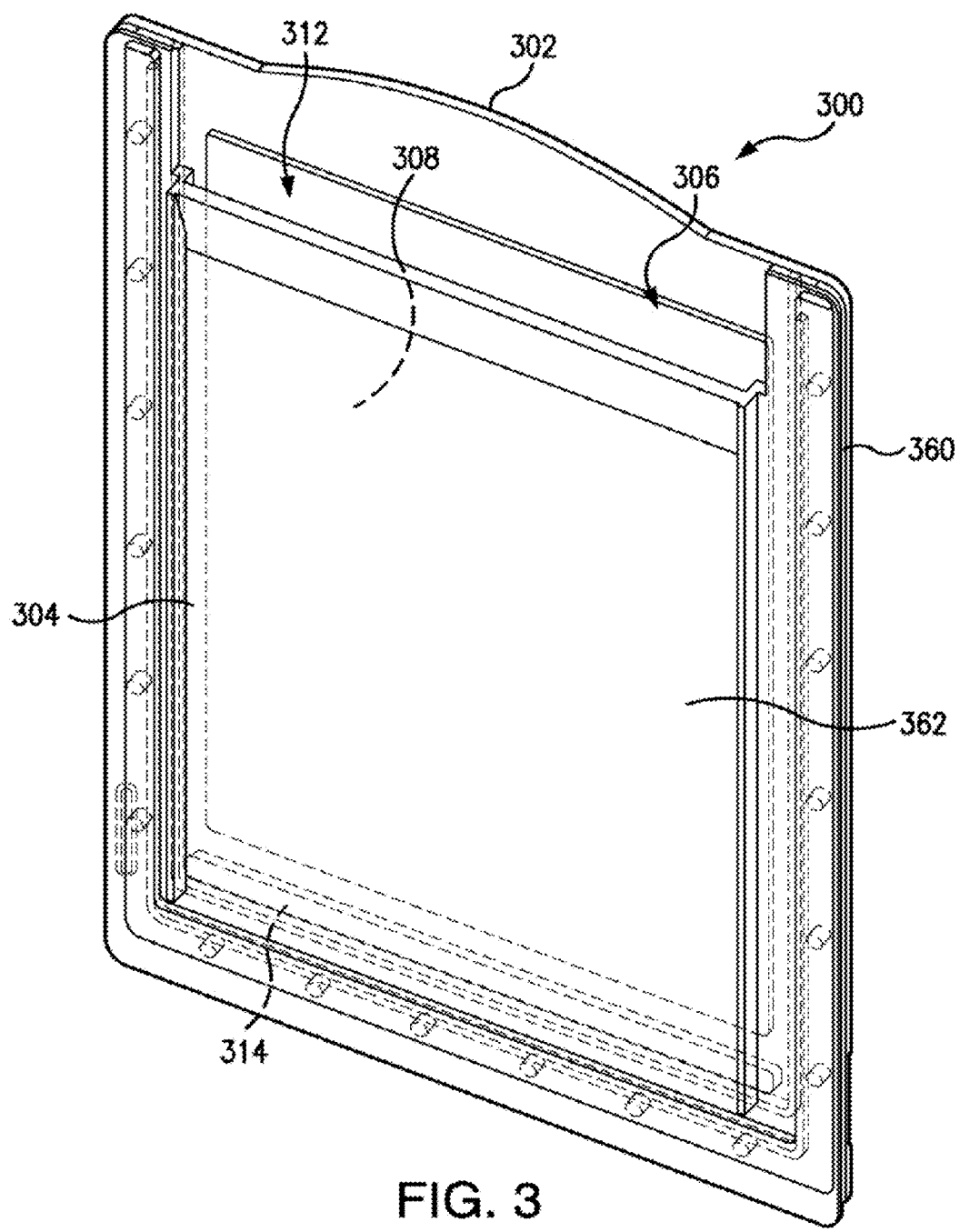
FIG. 3 shows an embodiment of an assembled gel cassette according to various embodiments of the present teachings.

An assembled cassette 300 formed from a retainer plate 304 and a divider plate 302 is shown in FIG. 3. An opening 312 created by joining of the retainer plate 304 and the divider plate 302 may be located at the top of the assembled cassette 300. In some embodiments, the opening 312 formed by the retainer plate 304 and the divider plate 302 is flat on one side while the other side of the opening is configured so that the opening of the assembled cassette may receive a comb having wedge shaped teeth or v-shaped teeth.

In some embodiments, the retainer plate 304 and the divider plate 302 may be fabricated as a single piece of plastic. In some embodiments, the retainer plate 304 and the divider plate 302 may be two separate parts that are connected together. The two separate parts may be connected together by any suitable mechanism for attaching the plates together including, for example purposes only, glue, pressure fitting, welding, adhesive, clamps, clips, or any other suitable mechanism.

During preparation of a gel, the slot 314 in the divider plate 302 may be sealed. The slot 314 may be sealed by any suitable sealant including tape, epoxy, glue, polymer compound, or any other suitable sealant. The sealant may or may not be a conductive sealant. In some embodiments, the sealant may be a permanent sealant or a removable sealant. Once the slot 314 has been sealed, the cassette 300 may be held vertically and gel-forming mixture is poured through the opening 312 into the cavity 362 formed between the retainer plate 304 and the divider plate 302. After the gel has been cast, an electric circuit may be formed either through a conductive sealant material, or alternatively, the sealant can be removed from the exterior of the cassette, thereby exposing the gel inside the cassette to a buffer solution and thereby completing the electric circuit path.

The gel mixture may be in contact with the interior surfaces 306, 308 of the divider plate 302 and the retainer plate 304, respectively. In some embodiments, the interior surfaces 306, 308 of the divider plate 302 and the retainer plate 304, respectively, may be coated. In some embodiments, the one or both of the interior surfaces 306, 308 of the plates may be coated with an oxygen interference coating such as $SiO_x$, for example, SiO or $SiO_2$, or any combination thereof or any other suitable coating, which may form an oxygen barrier that reduces diffusion from the surface of the plastic plates into the gel to prevent significant local variations in the rate of oxygen diffusion. Methods for coating plastic gel molds can be found in U.S. Pat. No. 5,685,967, which is incorporated herein by reference in its entirety. In some embodiments the coating may be substantially transparent. The interior surfaces 306, 308 may be coated manually or mechanically and in some embodiments where the cassette is formed from two separate plates, the coating may be performed before or after joining the plates into the cassette. In some embodiments, the interior surfaces 306, 308 of the cassette may be coated under vacuum using evaporation or vapor deposition, sputter deposition, chemical vapor deposition, plasma-enhanced chemical vapor deposition, or any combination thereof. In some embodiments, the coating deposited may be of a thickness less than about 5000 Angstroms in thickness.

In some embodiments, the gel cassettes are about 10 cm by 10 cm for mini-gel cassettes. The gels housed in the gel cassettes are about 7 cm in length (the running length) by about 8 cm wide. The gel cassettes and gels run in the gel cassettes may be any suitable length. In some embodiments, the assembled cassette may include a gap 360 that runs around the outer perimeter of the cassette 300. The gap 360 may facilitate the opening of the cassette for gel retrieval.

After the gel has been loaded with sample, the gel cassette containing the samples in the wells may be placed into an electrophoresis device that creates a liquid-tight seal between the external margins of the retainer and the divider plates. After being placed in the electrophoresis device, the electrode buffer is placed in the anode tank (formed behind the sealed divider) and the cathode tank (formed behind the sealed retainer). When a voltage is applied to the electrophoresis device anions flow from the cathode tank down through the sample wells and gel into the anode tank, while cations flow into the bottom, and through, the gel from the anode tank. The gel cassette may be used with any suitable electrophoresis device or system, including the system described in U.S. Provisional Application Ser. No. 61/237, 287, filed Aug. 26, 2009, the contents of which are incorporated by reference in their entirety.

II. Comb

Figure 4:
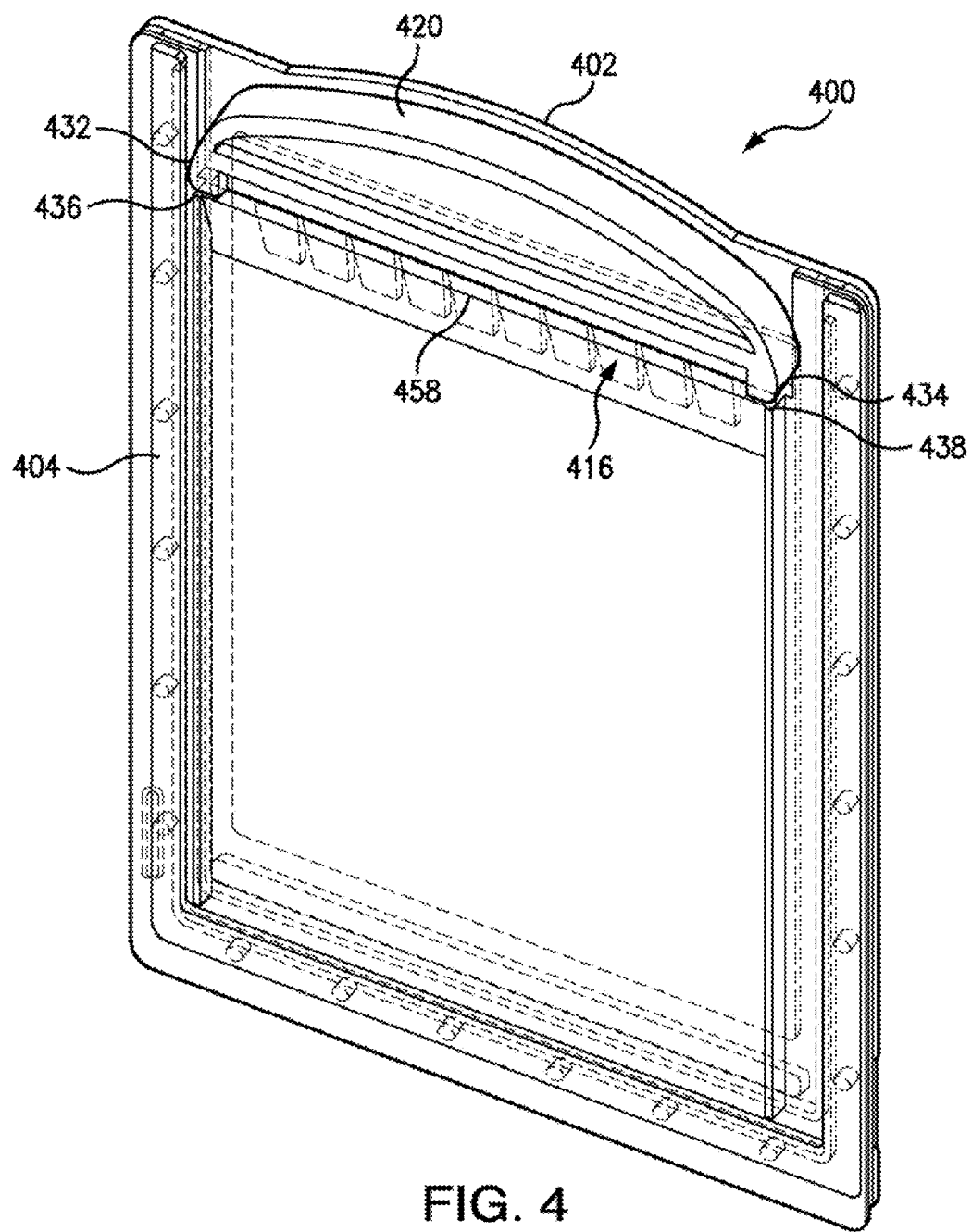
FIG. 4 shows an embodiment of a cassette and an embodiment of a comb according to various embodiments of the present teachings.

As shown in FIG. 4, once the gel material has been poured into the opening of an assembled cassette 400, a comb 420 may be inserted into the opening of the assembled cassette, so that the teeth of the comb contact the top portion of the gel material. The depth of insertion of the comb 420 may be limited by the edges 432, 434 of the comb 420 and the shoulders 436, 438 of the opening located on the cassette 400. In some embodiments, the depth of insertion of the comb 420 may be further limited by the comb 420 resting on the front edge 458 of the lip 416. Once the gel has been cast, the comb may then be removed leaving a void at the position of each tooth. The voids formed by the teeth of the comb are the sample wells in the gel.

Figure 5A:
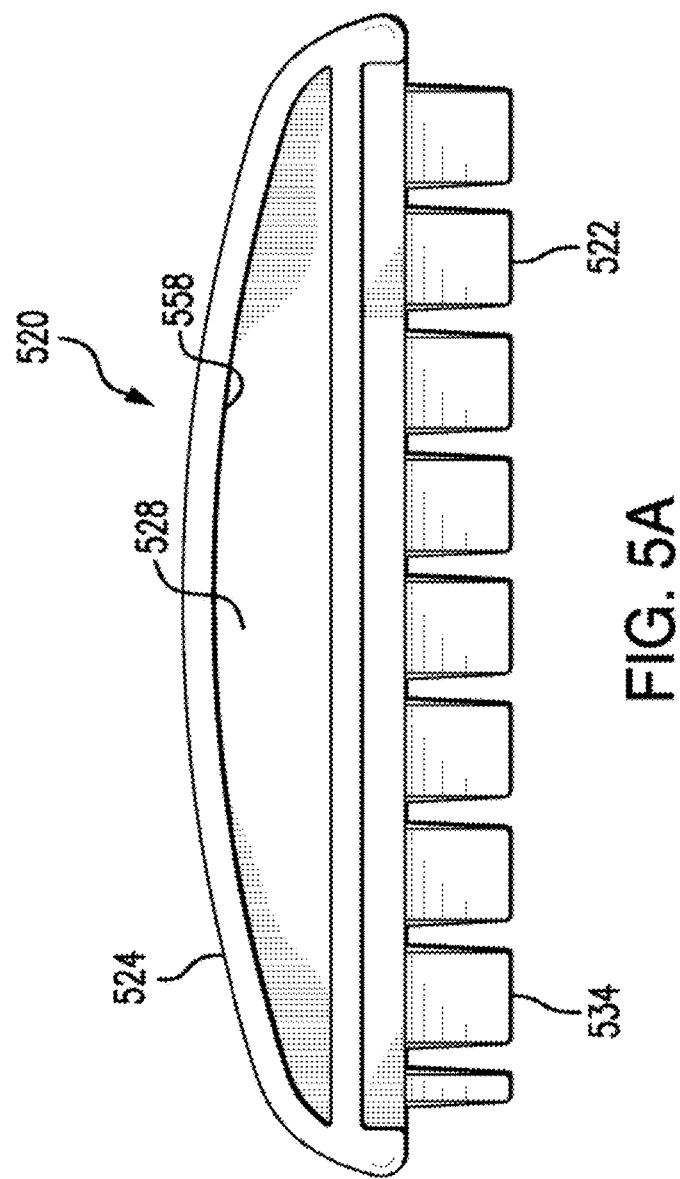
Figure 5B:
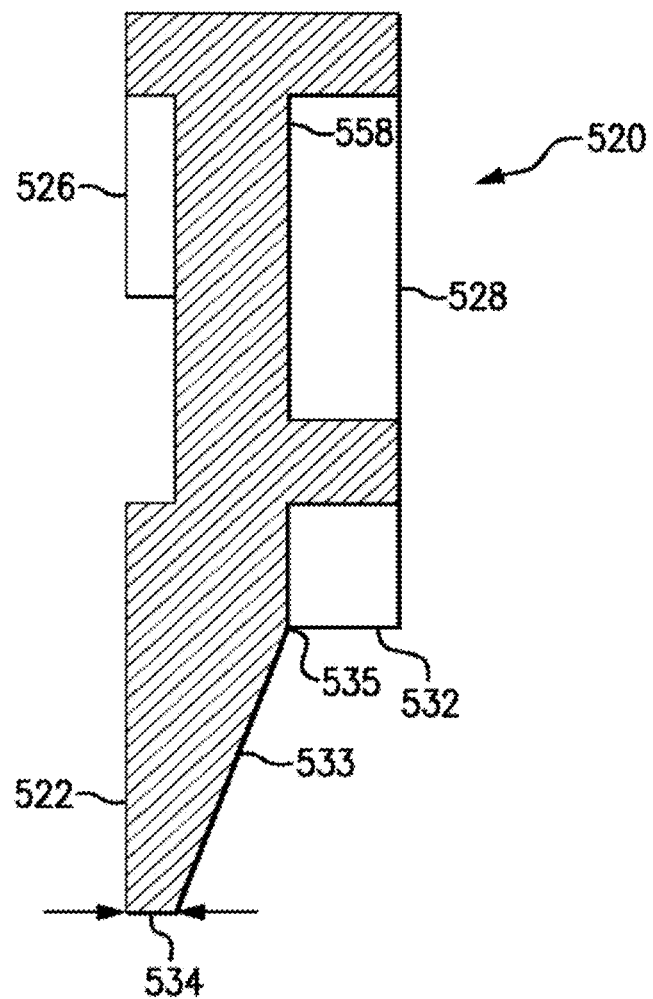

FIGS. 5A-5C show different views of an embodiment of a comb 520 to be used with a gel cassette provided herein. In some embodiments, the comb 520 may have wedge-shaped teeth 522, as shown in FIGS. 5A-5C. A comb 520 having wedge-shaped teeth 522 may be capable of creating wedge-shaped wells in the gel. The wedge-shaped wells created by insertion of the comb with wedge shaped teeth into the gel material may provide a larger opening to the well at the top and thereby create easier access to the wells using a standard pipette tip on a single pipette or on a multi-channel pipette. Additionally, the wedge-shaped wells permit a greater amount of sample to be loaded into a thinner gel (for example, approximately 1 mm thick gels). The comb 520 may be used with any of the cassettes described herein previously, or may be used with any other suitable cassette for creating a gel.

The wedge-shaped wells in the gel created by the wedge shaped teeth may be of a volume at least 10% greater than the volume of the wells created using a standard comb. In some embodiments, the wedge shaped wells may have a volume that is at least 20% greater, at least 50% greater, at least 100% greater, at least 150% greater, at least 175% greater, at least 200% greater, at least 250% greater than a well created using a standard comb. Additionally, the wedge-shaped wells allow for loading an increased amount of sample while maintaining or improving band sharpness and resolution during electrophoresis.

In some embodiments, the comb 520 is a nine-tooth comb, as shown in FIGS. 5A & 5C. In some embodiments, the comb may be at least a single tooth comb, at least a 2-tooth comb, at least a five-tooth comb, at least a seven-tooth comb, at least a 9-tooth comb, at least a ten-tooth comb, at least a twelve-tooth comb, at least a 15-tooth comb, at least a 17-tooth comb, at least a 20-tooth comb, or any other comb having a suitable number of teeth. In some embodiments, the comb may be molded from any suitable plastic including, but not limited to polymers such as polyethylene terephthalate, polyvinyl chloride, polymethyl methacrylate, polystyrene, polyethylene, polymethyl polypropylene, cellulose acetates, co-polymers, polycarbonate, or any other suitable material. In some embodiments, the dimensions of the teeth may be uniform along the length of the comb or the teeth may have varying dimensions along the length of the comb. The teeth 522 may or may not be the same shape as the wedge shaped opening of the cassette.

In some embodiments, the edge 520 of the comb located opposite to the teeth 522 may be a curved edge 524. The curved edge 524 may facilitate the insertion and removal of the comb 520 from the cassette. The comb 520 may further include a back surface 526 and a front surface 528. In some embodiments, the front 528 and back 526 surfaces are solid. The back surface 526 of the comb 520, may be flush with the interior surface 406 of the divider plate 402 (in FIG. 4), and the front surface of the comb 520 may be align with the front edge 458 of the lip 416 of the retainer plate 404 (shown in FIG. 4). In some embodiments, the front surface 528 of the comb 520 has a recessed space 558 which in conjunction with the back surface 526 of the comb 520 facilitates gripping the comb 520 to facilitate the insertion of the comb into the cassette by the user. The recessed space 558 may further assist in the removal of the comb 520 from the cassette by the user, once the gel and wells have been formed. In some embodiments of the comb, the comb has a recessed area in the back of the comb where the comb contacts the cassette. In some embodiments, the recessed area helps to eliminate polymerized gel formation in the sample wells of the electrophoresis gel. The recessed area helps prevent the formation of a "skin" in the sample wells during the gel casting process since the recessed area eliminates geometrically induced capillary forces. Additionally, the recessed area helps to make loading the sample problem free by preventing any gel material from being pushed into the sample well by the pipette tip as the sample is loaded into the well.

As shown in FIGS. 5A & 5C, in some embodiments the teeth 522 on the comb 520 may be fabricated such that the first and last well on the comb are located a suitable distance from the edges of the comb. By positioning the teeth a suitable distance from the edges of the comb, a gel can be created where the wells are located a suitable distance from the sides of the gel thereby increasing the quality, resolution, and sharpness, of the bands. Such a location of the wells reduces the chance that the bands formed in the gel will turn up at the ends of the band or "smile" or turn down at the ends of the band or turn down at the edges of the band or "frown" or otherwise deviate from the horizontal straightness and become more angled.

FIG. 5B shows a cross-sectional side view of comb 520 from FIGS. 5A and 5C. As seen in FIG. 5B, the wedge-shaped teeth 522 taper along the length of the tooth so that the well formed with the wedge comb 522 is wider at the top end of the gel and narrower or tapered at the bottom end of the well. The depth of the sample well formed in the gel is as deep as the height of the angled portion of the tooth 522 from the tip to the edge 532 of the comb and is further defined by the space between the angled-surface teeth.

In some embodiments, the bottom surface 534 of the wedge may be about 0.04 cm in depth (as indicated by the arrows). In some embodiment, the bottom surface 534 may be between about 0.03 inch and about 0.05 inch. The top of the tooth 535 may be about 0.18 inch. In some embodiments, the top of the tooth 535 may be between about 0.15 and about 0.2 inch. At least one surface 533 of the wedge may extend from a plane parallel to the bottom surface of the tooth at an angle of 70 degrees. In some embodiments, the at least one surface 533 may extend from the bottom surface plane at an angle of between about 45 degrees and about 90 degrees.

Figure 8A:
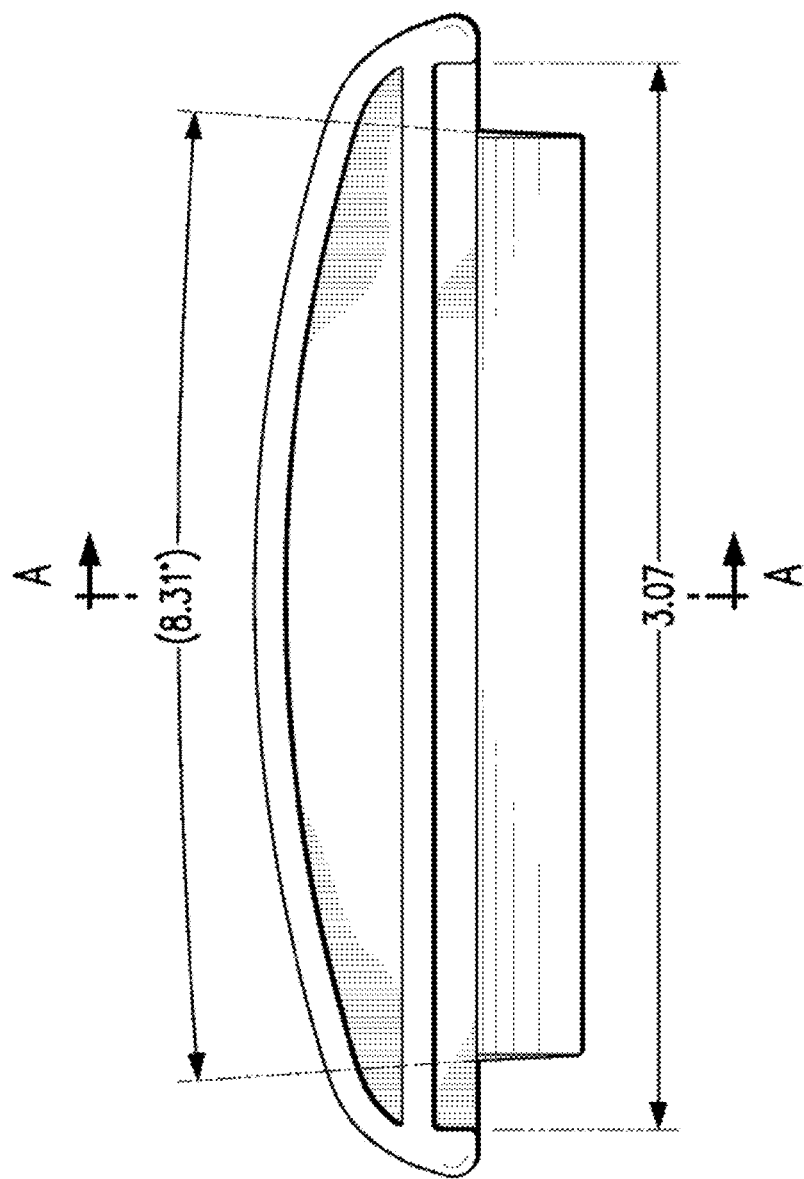
FIGS. 8A-8C are a side view, a cross-sectional view, and a bottom view, respectively, of a single well comb according to various embodiments of the present teachings.
Figure 8B:
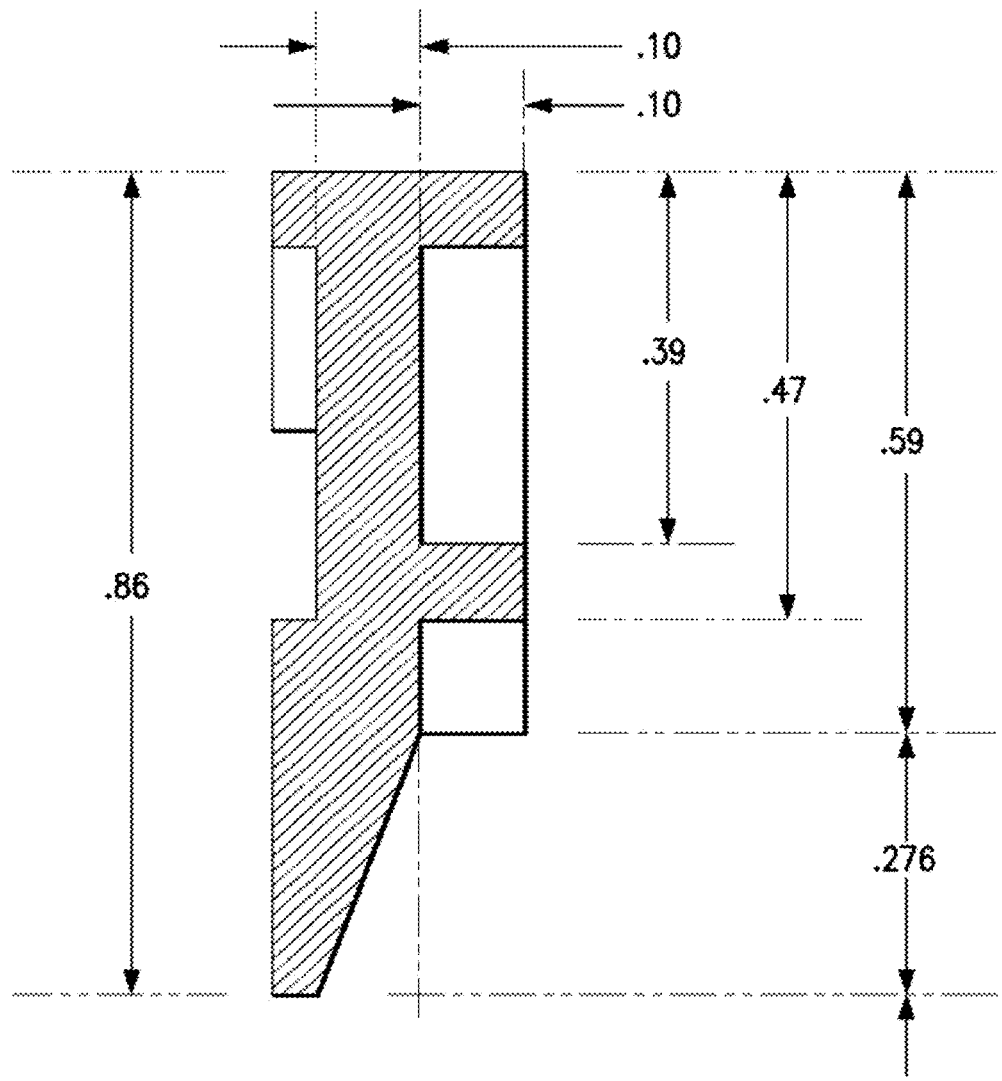
Figure 8C:
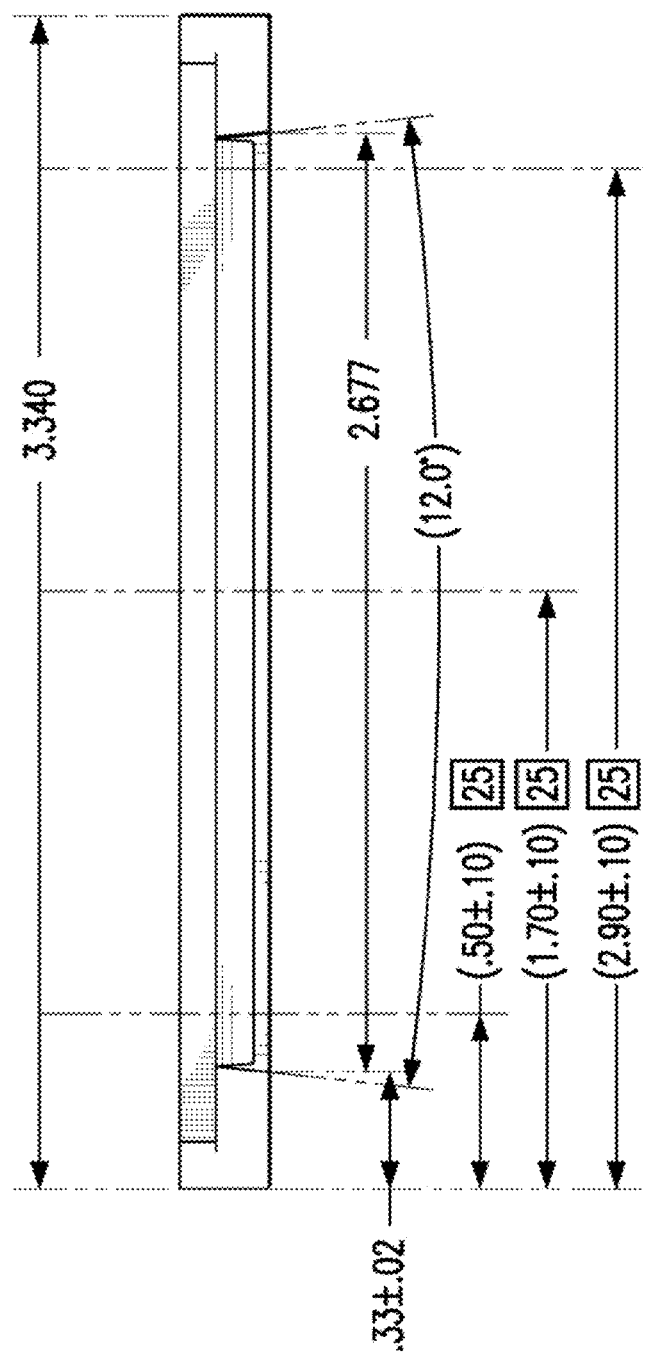

FIGS. 8A-8C are a side view, a cross-sectional view, and a bottom view, respectively, of a single well comb according to various embodiments of the present teachings, and show various dimensions in inches, and angles, that can be used for such a configuration. FIG. 8B is a cross-sectional view taken along line A-A shown in FIG. 8A.

Figure 9A:
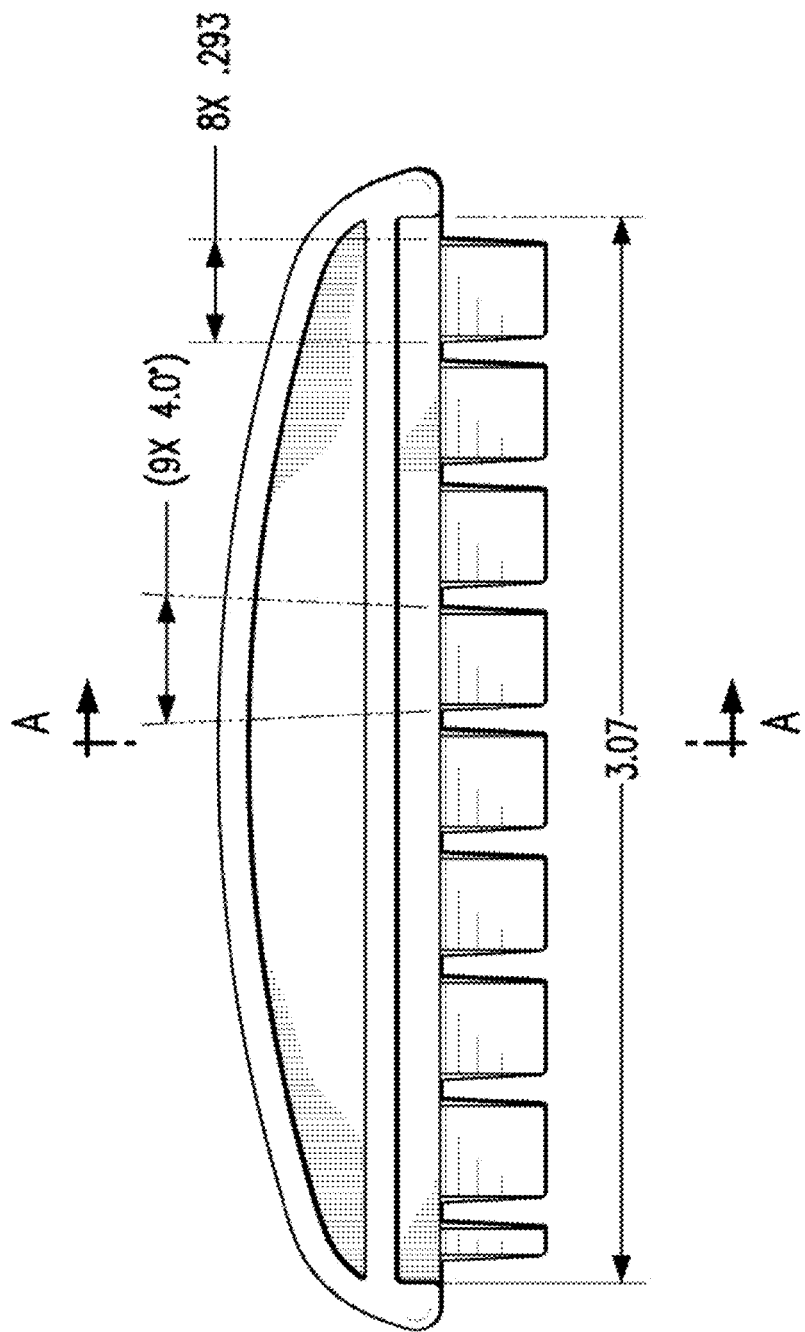
FIGS. 9A-9C are a side view, a cross-sectional view, and a bottom view, respectively, of a nine well comb according to various embodiments of the present teachings.
Figure 9B:
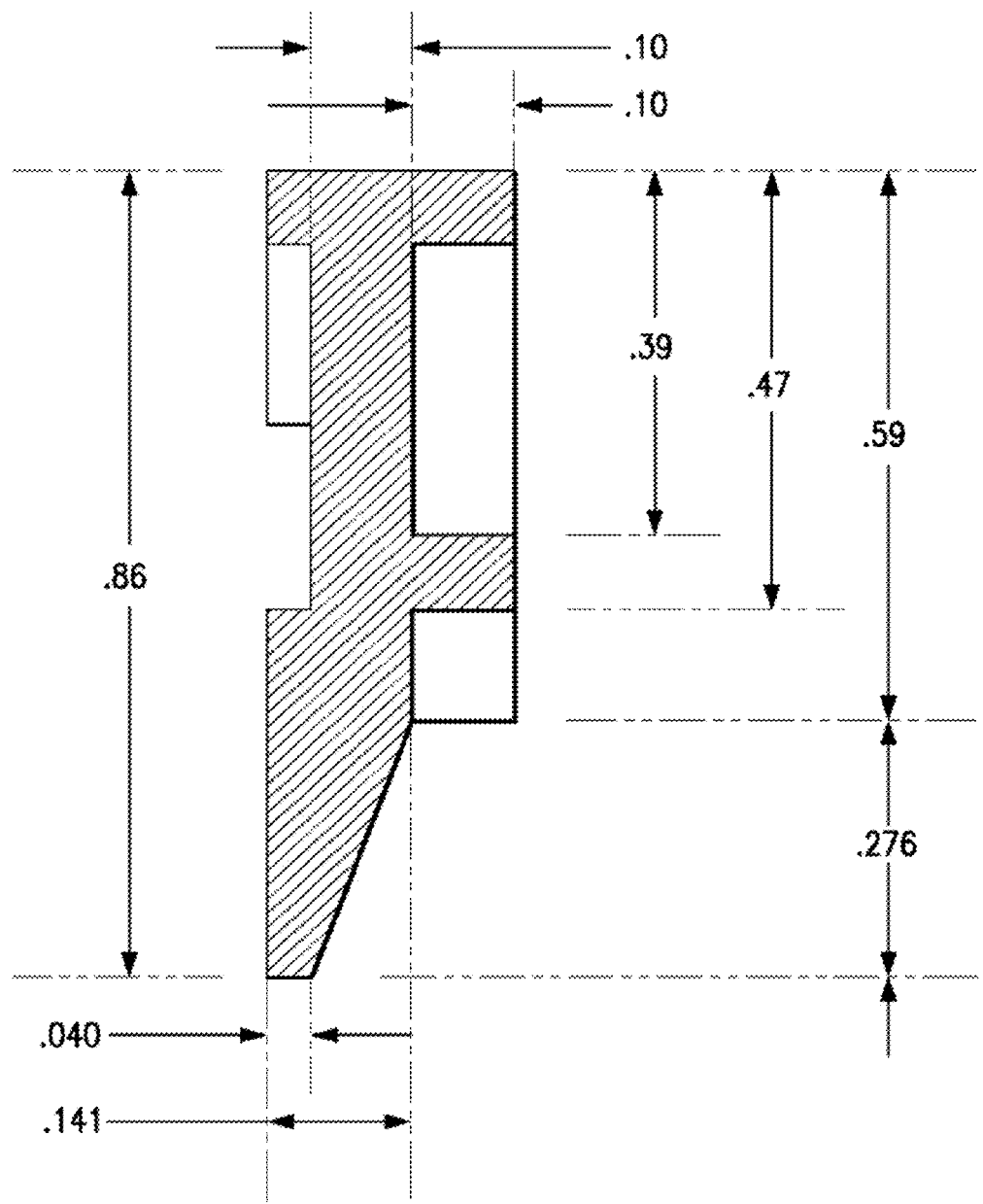
Figure 9C:
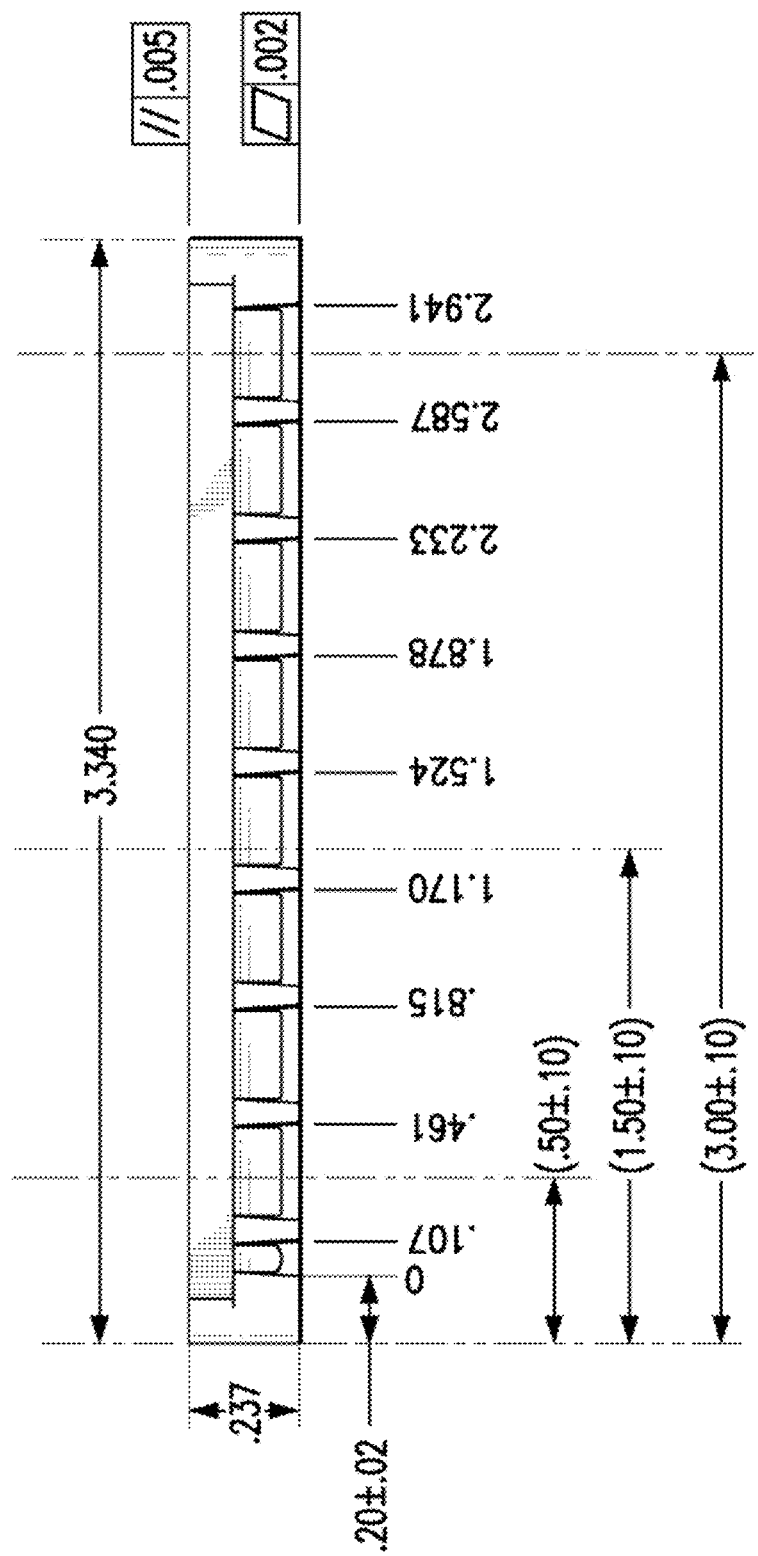

FIGS. 9A-9C are a side view, a cross-sectional view, and a bottom view, respectively, of a nine well comb according to various embodiments of the present teachings, and show various dimensions in inches, and angles, that can be used for such a configuration. FIG. 9B is a cross-sectional view taken along line A-A shown in FIG. 9A.

Figure 10B:
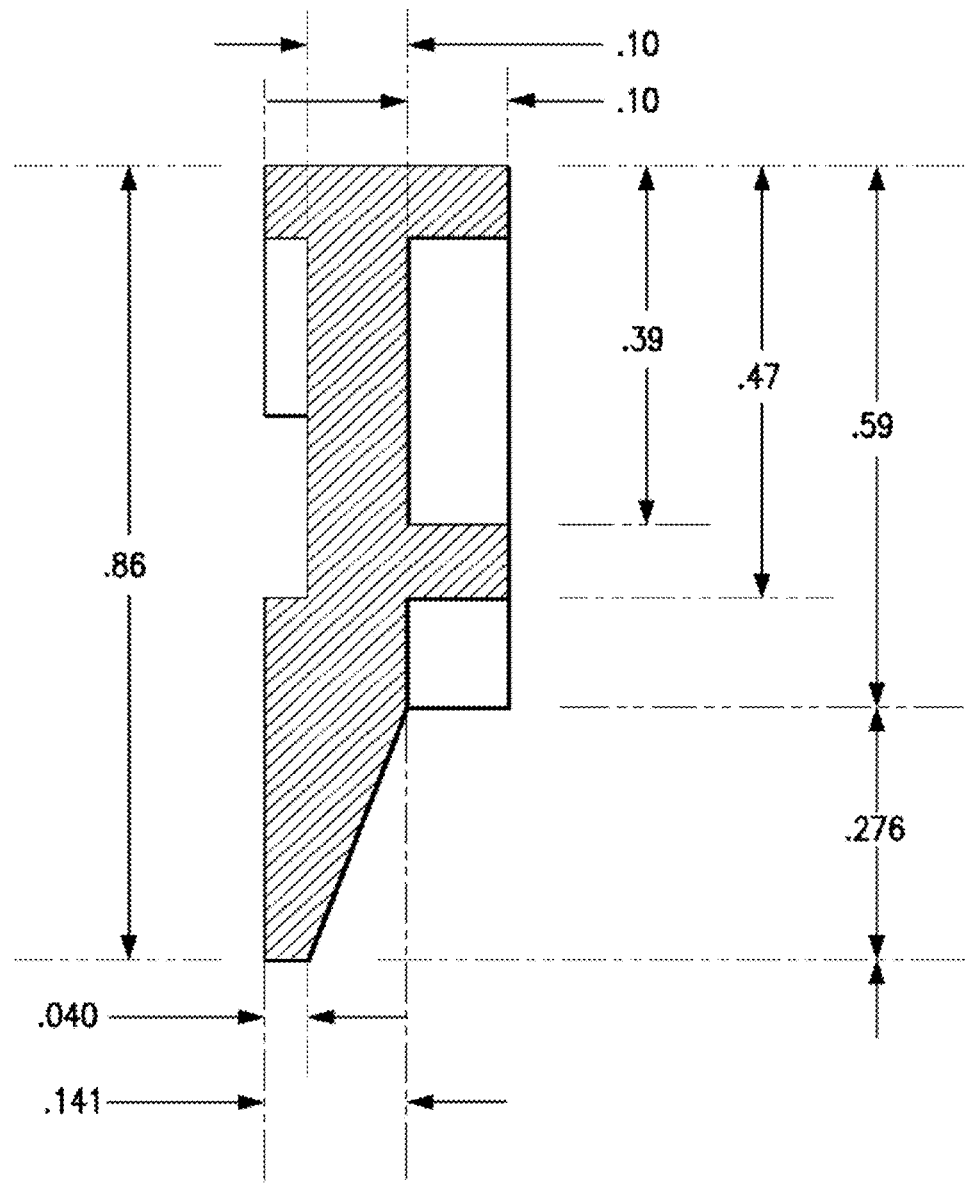
Figure 10C:
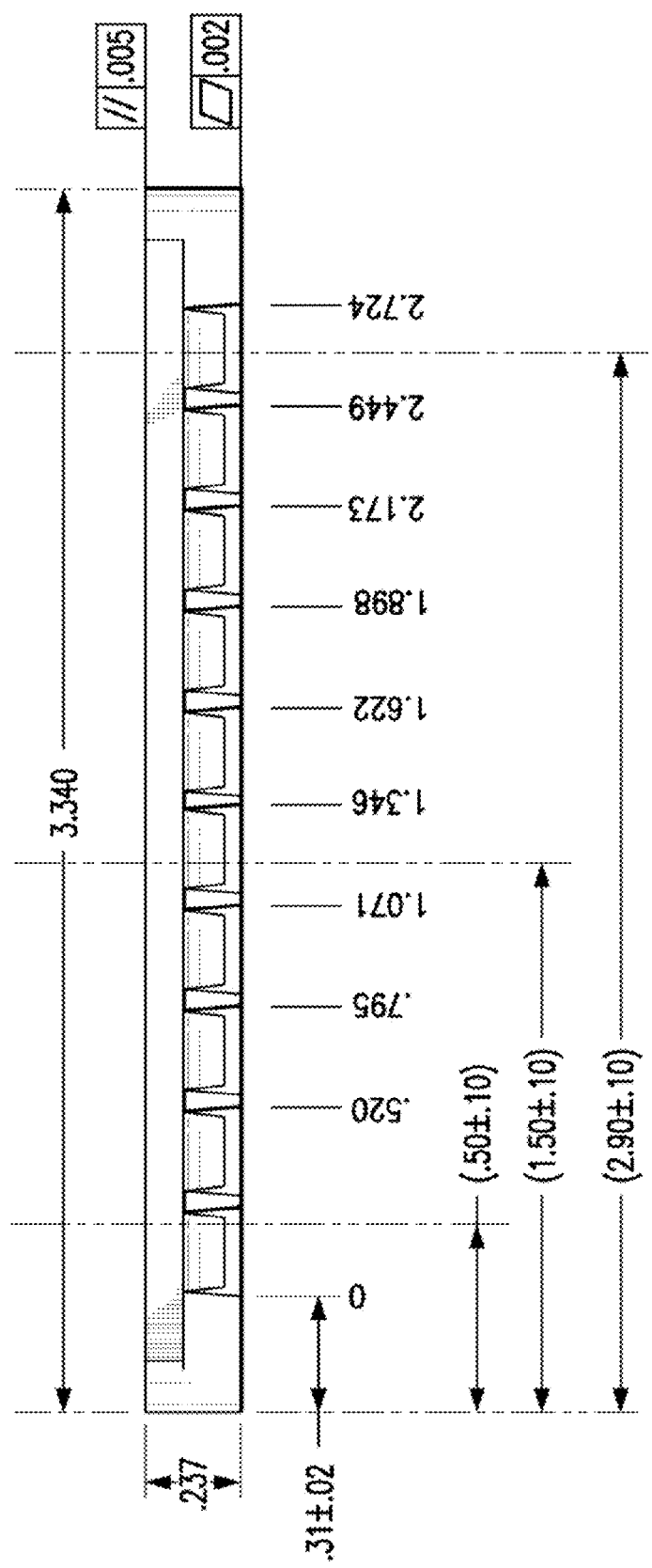

FIGS. 10A-10C are a side view, a cross-sectional view, and a bottom view, respectively, of a ten well comb according to various embodiments of the present teachings, and show various dimensions in inches, and angles, that can be used for such a configuration. FIG. 10B is a cross-sectional view taken along line A-A shown in FIG. 10A.

Figure 11A:
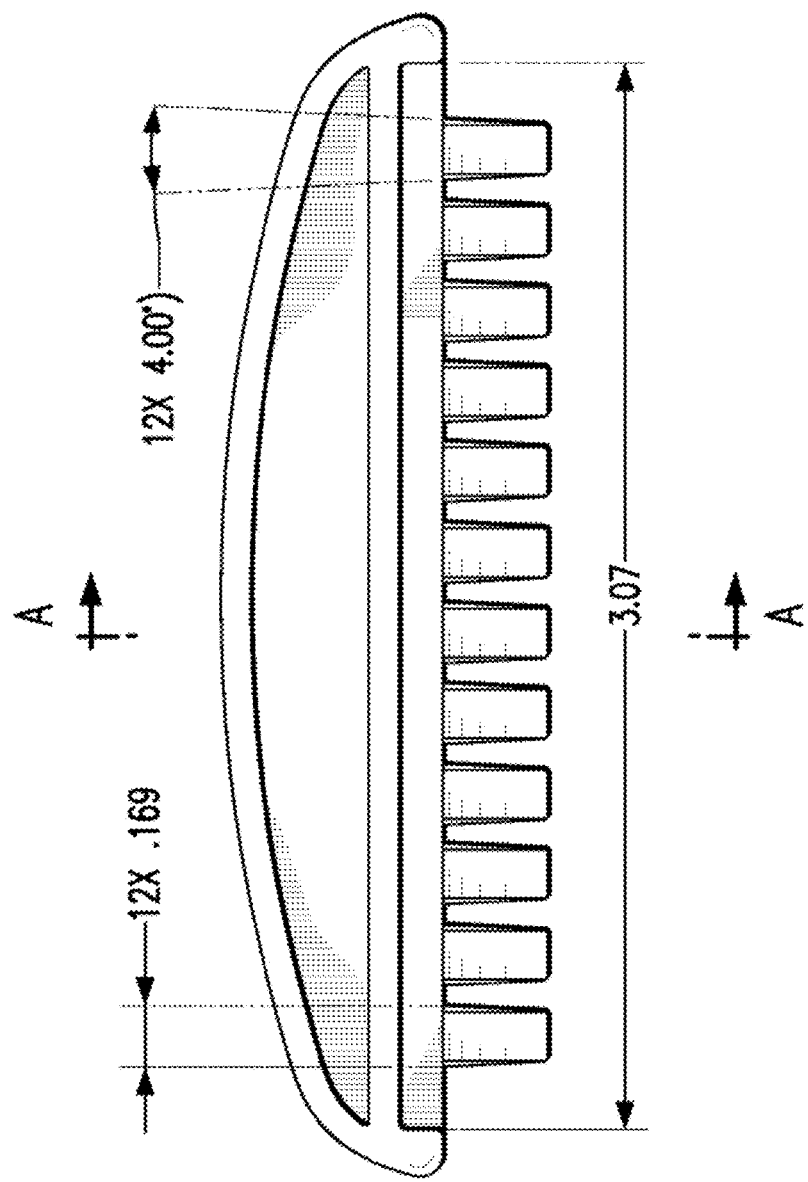
Figure 11B:
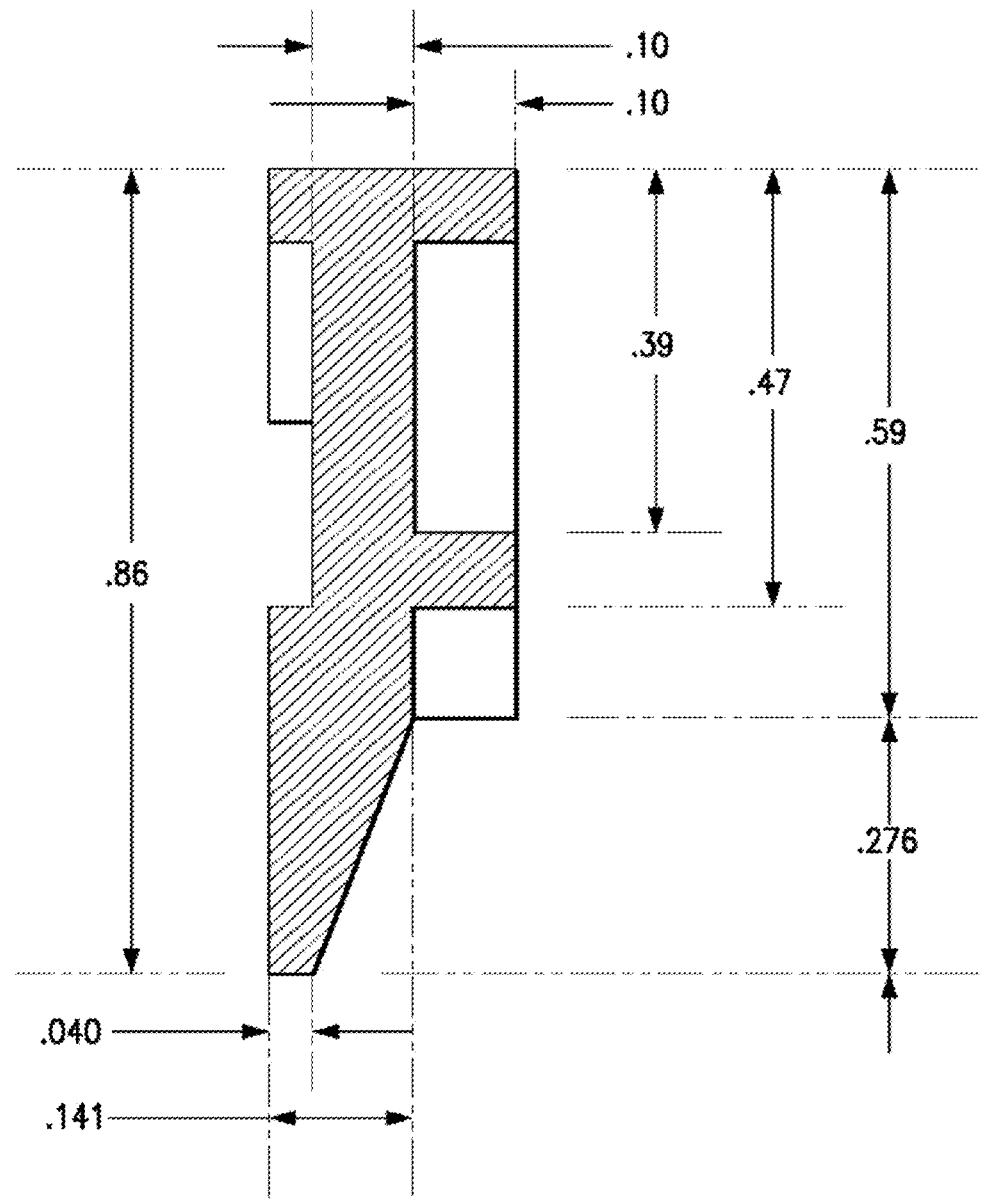
Figure 11C:
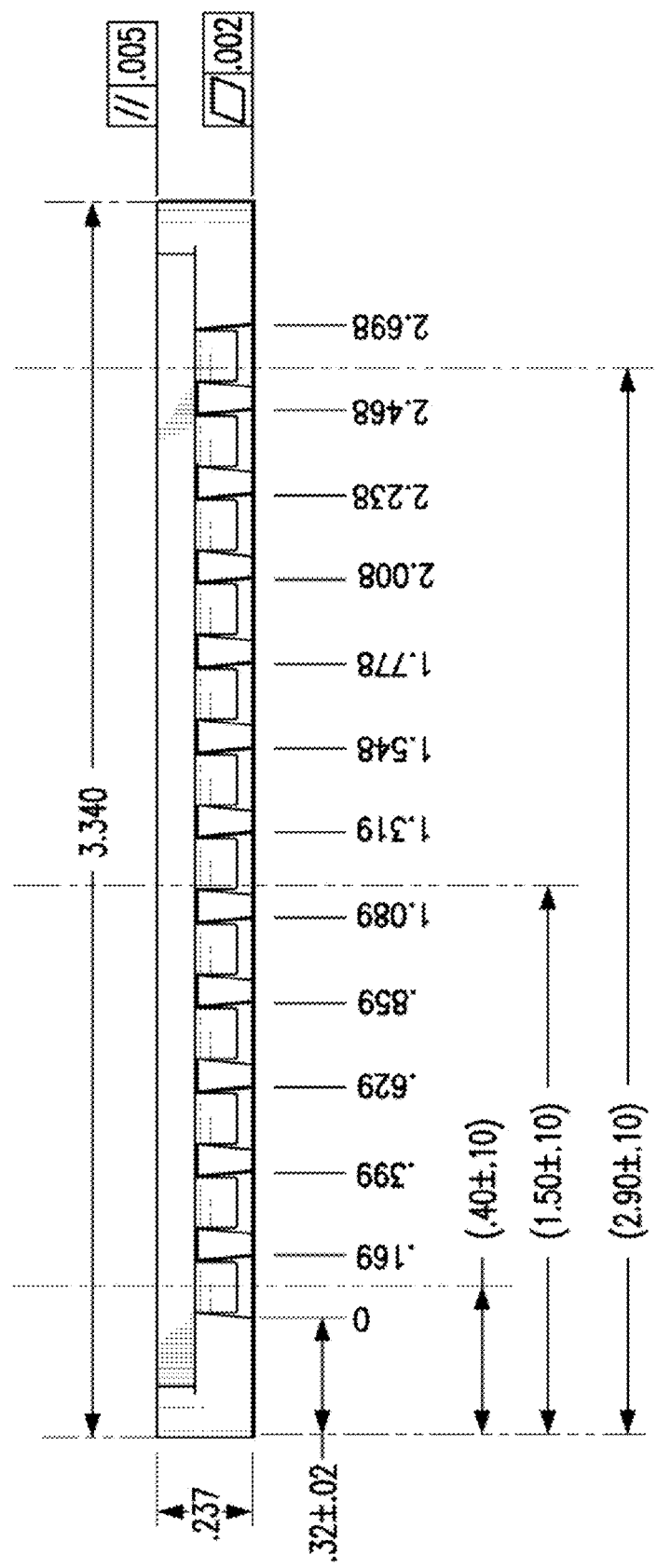

FIGS. 11A-11C are a side view, a cross-sectional view, and a bottom view, respectively, of a twelve well comb according to various embodiments of the present teachings, and show various dimensions in inches, and angles, that can be used for such a configuration. FIG. 11B is a cross-sectional view taken along line A-A shown in FIG. 11A.

Figure 12A:
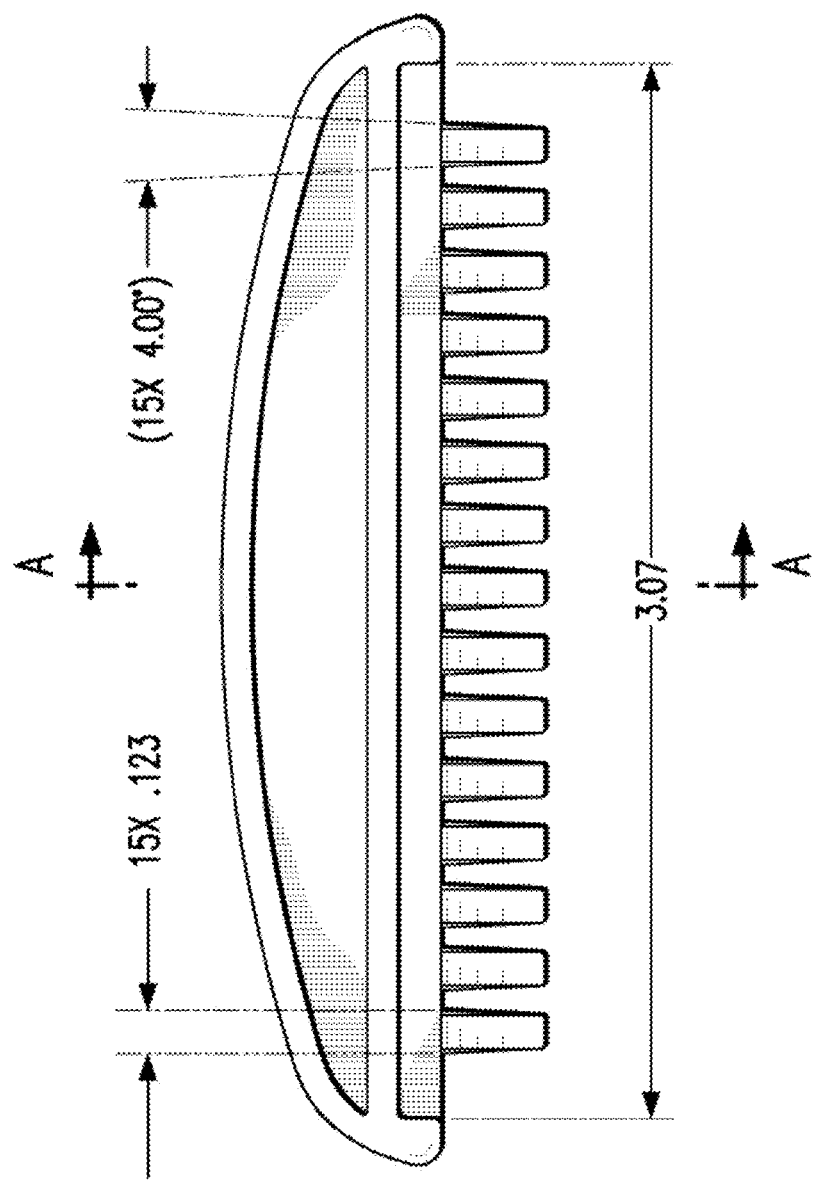
FIGS. 12A-12C are a side view, a cross-sectional view, and a bottom view, respectively, of a fifteen well comb according to various embodiments of the present teachings.
Figure 12B:
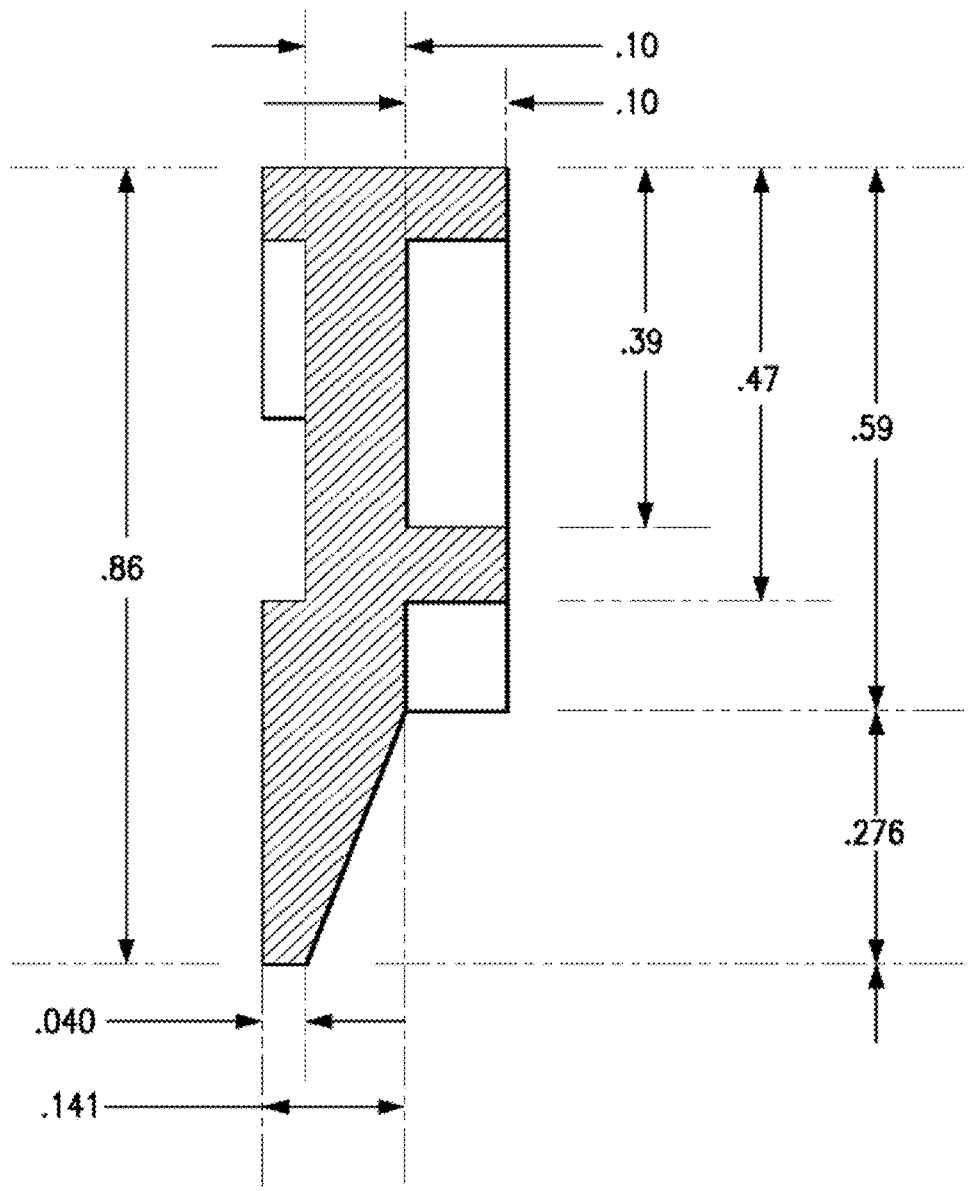
Figure 12C:
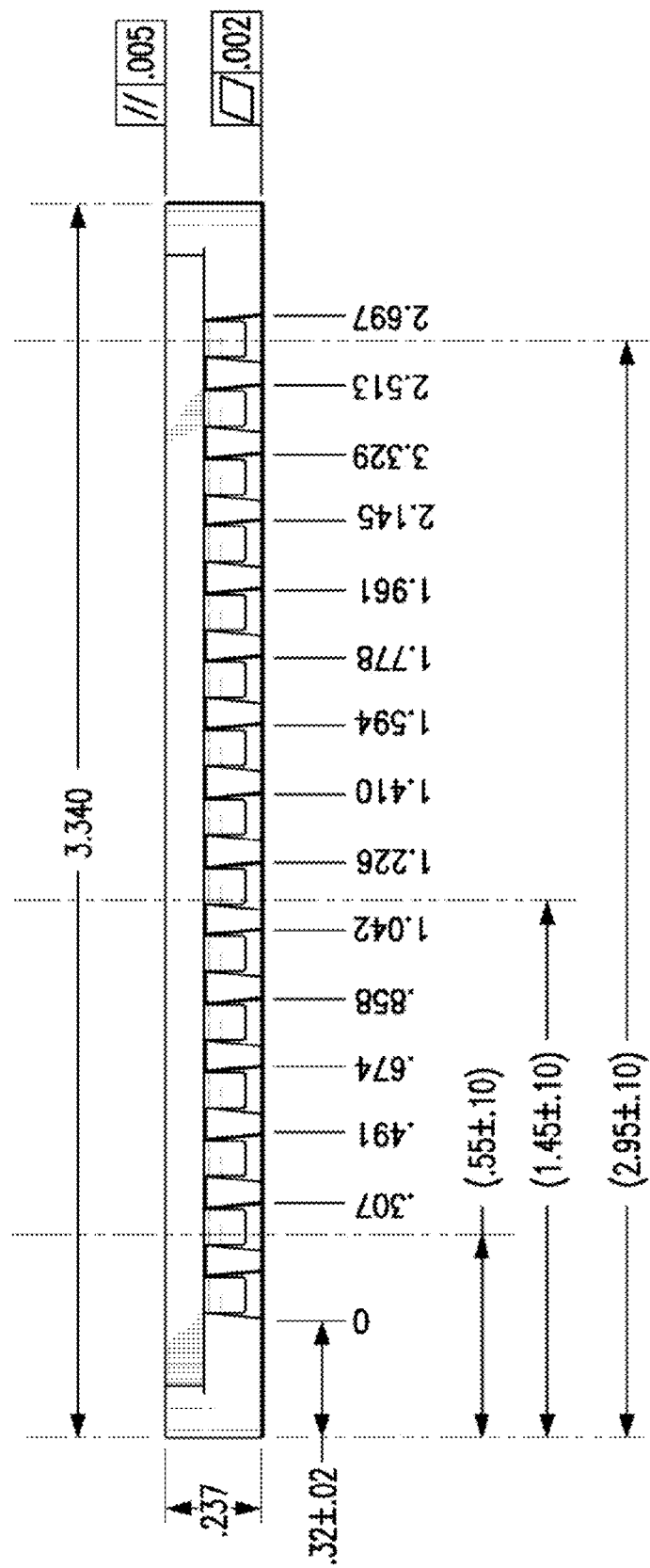

FIGS. 12A-12C are a side view, a cross-sectional view, and a bottom view, respectively, of a fifteen well comb according to various embodiments of the present teachings, and show various dimensions in inches, and angles, that can be used for such a configuration. FIG. 12B is a cross-sectional view taken along line A-A shown in FIG. 12A.

Figure 13A:
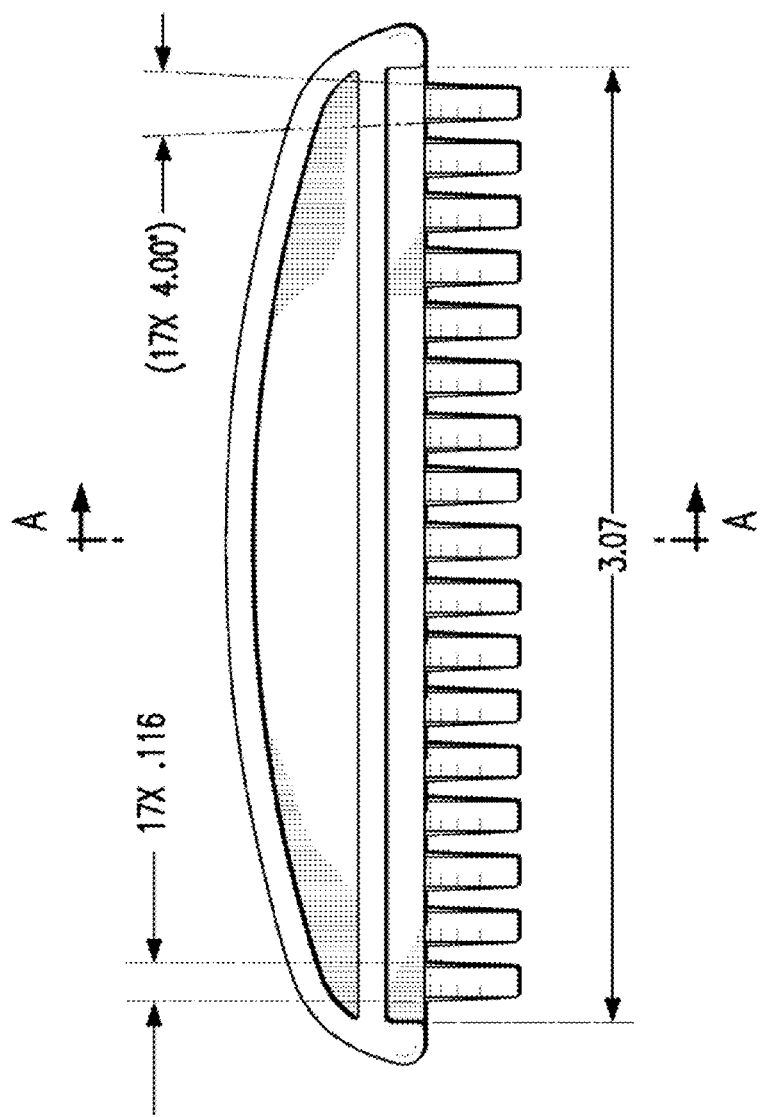
FIGS. 13A-13C are a side view, a cross-sectional view, and a bottom view, respectively, of a seventeen well comb according to various embodiments of the present teachings.
Figure 13B:
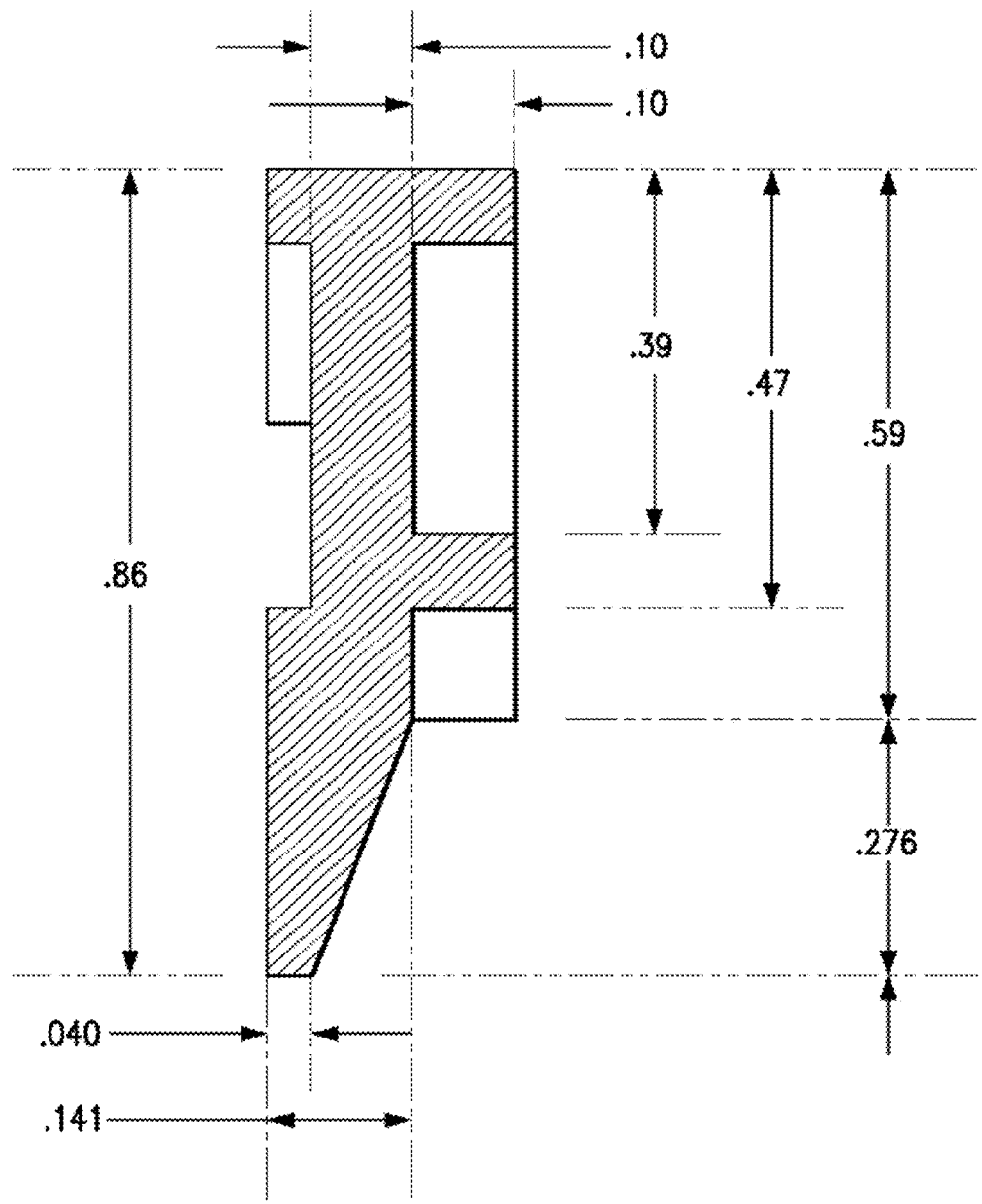
Figure 13C:
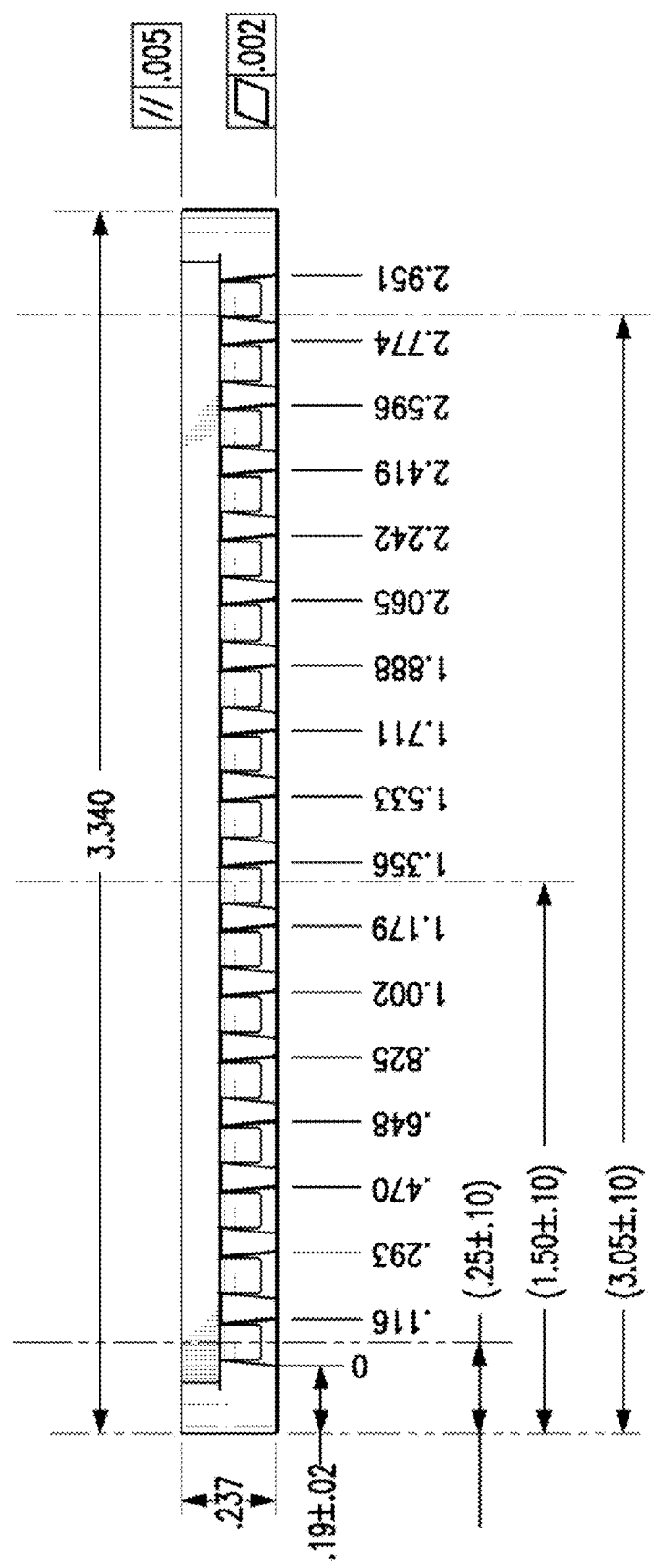

FIGS. 13A-13C are a side view, a cross-sectional view, and a bottom view, respectively, of a seventeen well comb according to various embodiments of the present teachings, and show various dimensions in inches, and angles, that can be used for such a configuration. FIG. 13B is a cross-sectional view taken along line A-A shown in FIG. 13A.

Figure 6A:
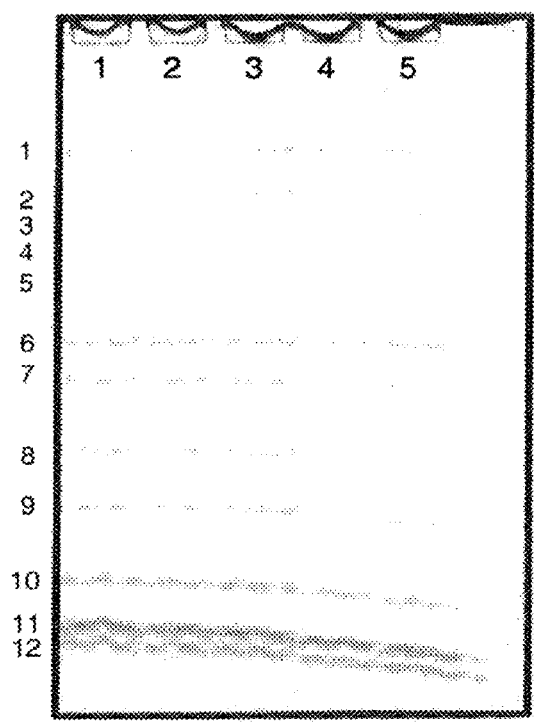
FIGS. 6A & 6B show images of gels.
Figure 6B:
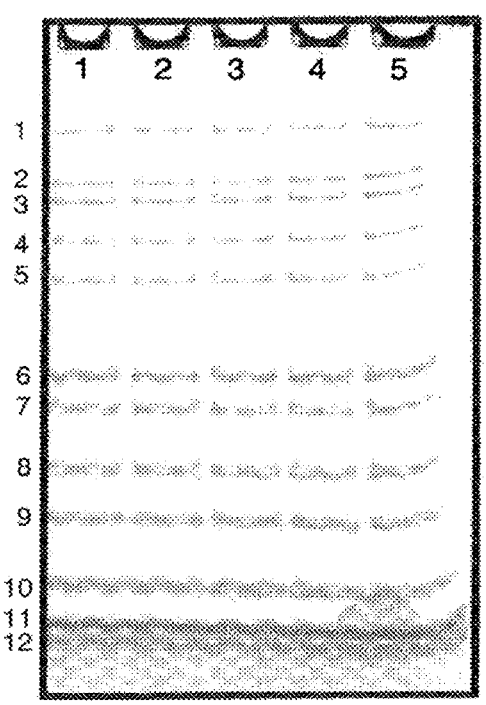

III. Examples 4-12% gels, as described in U.S. Provisional Application No. 61/236,293, filed Aug. 24, 2009, which is incorporated by reference in its entirety, were cast using a standard NOVEX® 1.5 mm Mini cassette and comb and using a test 1.0 mm wedge-well cassette and comb described herein in FIGS. 1-4 and 10A-10C. The gel in the NOVEX® cassette was cast using a standard (flat) 1.5 nm, 10-well comb. The gel in the test cassette was cast using a 10-well wedge shaped comb. Five lanes of each the NOVEX® cassette gel and the test cassette gel were loaded with 5 µL of MARK 12™ unstained standard diluted with NuPAGE® Sample Buffer to a final volume of 37.5 µL. In each of the five lanes of each gel, 37.5 µL of diluted standard was loaded, so that the performance of the gels could be evaluated by comparing volume of standard loaded into the gels. Each gel was run individually at 150 mA. The wedge well gel was run for 15 min and the 1.5 mm gel was run for 21 minutes. Upon completion of the runs, the gels were stained using SIMPLY BLUE SAFESTAIN, imaged on a flatbed scanner, and analyzed using NonLinear Dynamics Total Lab Software Version TL100. The software was used for the purpose of analyzing band sharpness. The band sharpness was measured using the automatic function for the generation of peaks, where the software determines the peak's start and end points. The difference between the end point and start point of the peak correlates to the band sharpness and is reported in millimeters. The results show that the bands on a 1.0 mm wedge well gel (FIG. 6A) are as sharp as the bands on a 1.5 mm standard mini gel (FIG. 6B). In some embodiments, the sample may be stained by any suitable stain and staining procedure, including those described in U.S. patent application Ser. No. 12/122,607, filed May 16, 2008 and U.S. Provisional Application No. 61/236,795, filed Aug. 25, 2009, which are both incorporated herein by reference in their entireties.

Figure 7:
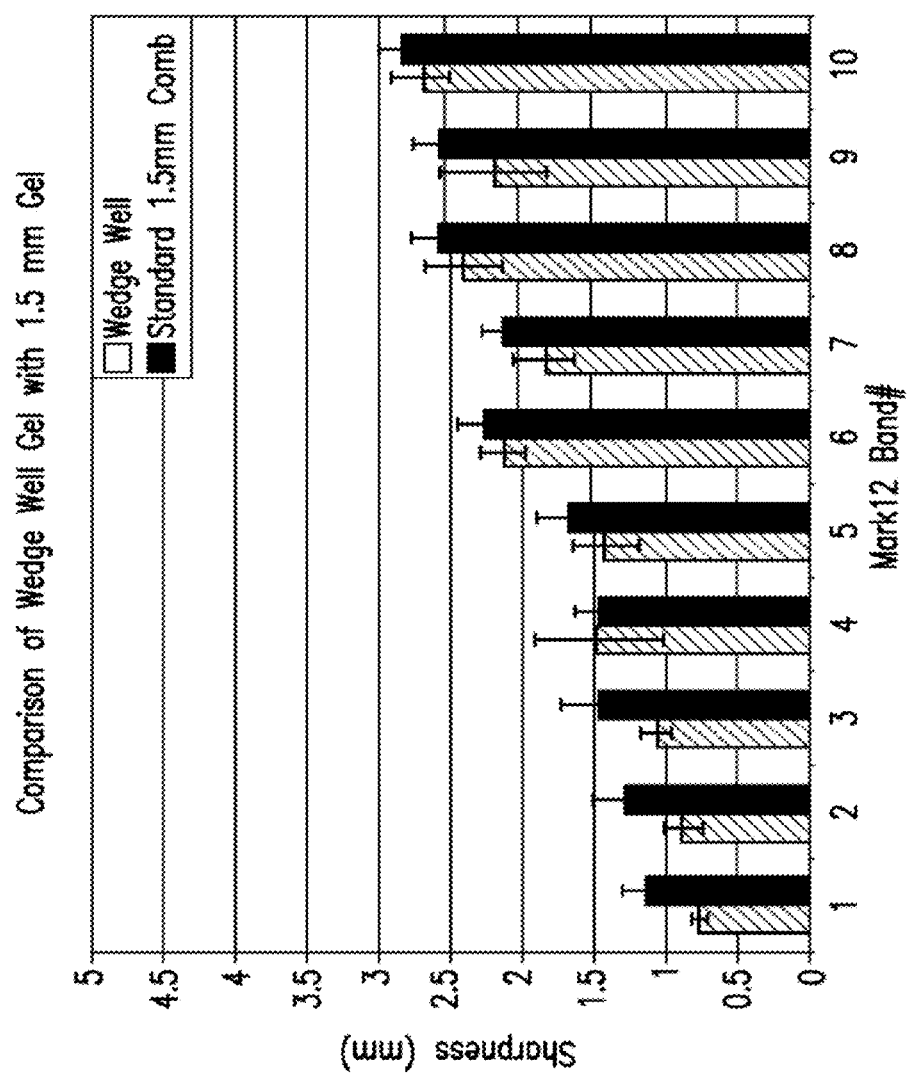
FIG. 7 shows a comparison of results from two different gel types.

FIG. 7 shows the comparison between the band sharpness using the 1.5 mm Mini cassette gel and standard comb and the wedge-well cassette and comb for diluted MARK 12 standard. Although the MARK 12 standard contains 12 bands, only the first ten bands were analyzed or compared in each lane. Some of the bands of the MARK 12 standard appear wavy on the 1.5 mm gel, particularly at the edge of the gel. The bands compared are as indicated in FIGS. 6A & 6B. The sharpness of the band across all five wells (n=5) and standard deviation is indicated on the y-axis and the band position along the x-axis. FIG. 7 shows a generally increased performance using the test cassette versus using the NOVEX® cassette.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for gel electrophoresis comprising:
a gel cassette, said gel cassette being configured to accommodate an electrophoresis gel, wherein the gel cassette comprises a retainer plate and a divider plate and a lip extends from the exterior surface of the divider plate or the retainer plate; and
a comb having at least one wedge-shaped tooth, the wedge-shaped tooth having a first thickness at the proximal end of the tooth and a second thickness at the distal end of the tooth, said first thickness being greater than said second thickness, wherein the comb comprises a recessed area on the comb, wherein the recessed area is configured to prevent the formation of a skin during gel formation
wherein an angled surface of the wedge-shaped tooth extends at an angle from the distal end to the proximal end of the tooth thereby defining a wedge shape,
wherein said at least one wedge-shaped tooth is configured to form a wedge-shaped sample well in said electrophoresis gel such that when said comb is removed, a void formed by said wedge-shaped tooth defines a sample well in said electrophoresis gel.

2. The apparatus of claim 1, wherein the ratio of the first thickness to the second thickness is 0.141/0.04.

3. The apparatus of claim 1, wherein the at least one wedge-shaped tooth has a volume of at least 40 µL.

4. The apparatus of claim 1, wherein the cassette has at least one interior surface and wherein the at least one interior surface is coated with a coating.

5. The apparatus of claim 1, wherein the coating is an oxygen interference coating and wherein the oxygen interference coating is selected from at least one of SiO or $SiO_2$.

6. The apparatus of claim 1, wherein the gel cassette has a lip extending at an angle from at least one exterior surface of the cassette.

7. The apparatus of claim 6, wherein said lip is complementary to said angled surface during use.

8. The apparatus of claim 1, wherein the sample well size is at least 10% larger than a gel having a sample well created by a standard comb, the sample well created by the standard comb having a volume of 37.5 µL.

9. The apparatus of claim 8, wherein the sample well size is at least 100% larger than a gel having a sample well created by a standard comb.

10. The apparatus of claim 1, wherein the comb ten wedge-shaped teeth configured to create a sample well in a gel.

11. The apparatus of claim 1, wherein the comb has wedge-shaped teeth configured to create sample wells configured to receive at least 10% more sample than a standard gel sample well, the standard gel sample well having a volume of 37.5 µL.

12. The apparatus of claim 1, wherein the apparatus is configured to create a gel having sharp bands.

13. The apparatus of claim 1, wherein the apparatus is configured to create a gel having high resolution.

14. The apparatus of claim 1, wherein the gel cassette has a cavity and the wedge-shaped tooth has at least one side that is slanted.

15. The apparatus of claim 14, wherein the at least one tooth is located at least 8.509 mm from the edge of the cavity.

16. The apparatus of claim 1, wherein the sample well has a volume of at least 70 µL.

17. The apparatus of claim 1, wherein the angled surface of the wedge-shaped tooth extends from a plane parallel to the bottom surface of the wedge-shaped tooth.

18. The apparatus of claim 17, wherein the angle of the surface relative to the plane parallel to the bottom surface is 70 degrees.

* * * * *